US008204760B2

(12) United States Patent
Cervi et al.

(10) Patent No.: US 8,204,760 B2
(45) Date of Patent: Jun. 19, 2012

(54) SYSTEMS, METHODS, AND COMPUTER PROGRAM PRODUCTS FOR FACILITATING COMMUNICATIONS, WORKFLOW, AND TASK ASSIGNMENTS IN MEDICAL PRACTICES AND CLINICS

(75) Inventors: Mark R. Cervi, Greenville, NC (US); Gary G. Leonhardt, Macclesfield, NC (US); James L. Crouch, Raleigh, NC (US)

(73) Assignee: Eflag Professional Solutions, LLC, Greenville, NC (US)

( * ) Notice: Subject to any disclaimer, the term of this patent is extended or adjusted under 35 U.S.C. 154(b) by 1283 days.

(21) Appl. No.: 11/701,695

(22) Filed: Feb. 2, 2007

(65) Prior Publication Data

US 2007/0185736 A1    Aug. 9, 2007

Related U.S. Application Data

(60) Provisional application No. 60/765,831, filed on Feb. 7, 2006.

(51) Int. Cl.
*G06Q 10/00* (2006.01)
*G06Q 50/00* (2006.01)

(52) U.S. Cl. .............................. 705/2; 705/3
(58) Field of Classification Search ................ 705/1–3; 704/270; 604/891.1
See application file for complete search history.

(56) References Cited

U.S. PATENT DOCUMENTS

| | | | |
|---|---|---|---|
| 4,991,091 A | 2/1991 | Allen | |
| 6,047,259 A | 4/2000 | Campbell et al. | |
| 6,259,657 B1 * | 7/2001 | Swinney | 704/270 |
| 6,314,405 B1 | 11/2001 | Richardson | |
| 6,711,547 B1 | 3/2004 | Glover | |
| 2002/0019749 A1 * | 2/2002 | Becker et al. | 705/2 |
| 2002/0026329 A1 * | 2/2002 | Saito et al. | 705/3 |
| 2002/0032582 A1 * | 3/2002 | Feeney et al. | 705/2 |
| 2002/0035487 A1 | 3/2002 | Brummel et al. | |
| 2002/0116219 A1 | 8/2002 | Ibok et al. | |
| 2003/0065308 A1 * | 4/2003 | Lebel et al. | 604/891.1 |
| 2003/0212581 A1 | 11/2003 | Adolph et al. | |
| 2004/0030987 A1 * | 2/2004 | Manelli | 715/500 |
| 2004/0039602 A1 | 2/2004 | Greenberg et al. | |
| 2004/0044546 A1 | 3/2004 | Moore | |
| 2004/0078211 A1 * | 4/2004 | Schramm-Apple et al. | 705/1 |
| 2004/0111296 A1 | 6/2004 | Rosenfeld et al. | |
| 2004/0189471 A1 * | 9/2004 | Ciarcia et al. | 340/572.1 |
| 2004/0220830 A1 | 11/2004 | Moreton et al. | |
| 2005/0033603 A1 | 2/2005 | Suzuki et al. | |
| 2005/0055242 A1 * | 3/2005 | Bello et al. | 705/2 |

* cited by examiner

*Primary Examiner* — Luke Gilligan
*Assistant Examiner* — Joseph Burgess
(74) *Attorney, Agent, or Firm* — Myers Bigel Sibley & Sajovec, P.A.

(57) ABSTRACT

A method of facilitating patient examinations in a medical office includes the following steps performed via a handheld device: identifying an examination location of a patient; identifying one or more medical procedures to be performed, wherein the one or more medical procedures are selected from the group consisting of: laboratory analysis of biological samples obtained from the patient, diagnostic tests on the patient, patient vaccinations and/or injections, and preparing a medical prescription; displaying a patient examination summary, wherein the displayed summary includes patient identification information, patient location information, patient health status information, and a list of identified medical procedures; and communicating wirelessly the patient examination summary to a nurse station computer within the medical office.

37 Claims, 21 Drawing Sheets

Figure 16

SYSTEMS, METHODS, AND COMPUTER PROGRAM PRODUCTS FOR FACILITATING COMMUNICATIONS, WORKFLOW, AND TASK ASSIGNMENTS IN MEDICAL PRACTICES AND CLINICS

RELATED APPLICATION

This application claims the benefit of and priority to U.S. Provisional Patent Application No. 60/765,831 filed Feb. 7, 2006, the disclosure of which is incorporated herein by reference as if set forth in its entirety.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

FIELD OF THE INVENTION

The present invention relates generally to health care and, more particularly, to health care information technology.

BACKGROUND OF THE INVENTION

Billions of dollars are spent yearly on health care information technology. New methods and software applications have been introduced to streamline information handling and reduce overhead expenditures for the healthcare industry. Medical practices and clinics have implemented new information technologies in various ways. For example, practice management software is fairly ubiquitous. Electronic medical records are becoming adopted, but very slowly. For example, electronic medical records have presently been adopted by only between about 10-15% of medical practices and clinics. The use of personal digital assistants (PDAs) has increased among physician groups for various functions, such as textbook references, medication cross-references and interactions, prescription writing, e-mails, web browsing, office schedules, and file sharing of patient medical records. However, applications that perform these functions may not work in concert and/or effectively with each other and may be cumbersome and time consuming to a physician.

Communication within medical practices and clinics is very important, particularly between physicians and medical staff. For example, it is important that physicians and medical staff be able to clearly communicate with each other about diagnostic testing, laboratory tests, and other ancillary services performed. Unfortunately, communication between physicians and medical staff can be difficult and sometimes chaotic. In some medical offices, devices are set up outside each exam room that help physicians communicate with the medical staff. An example of some devices include a plastic flagging system in which various color plastic pieces (flags) are turned outward indicating specific diagnostic testing which need to be for a particular patient. Other more advanced offices may utilize a series of lights on a wall which indicate the need for specific tests. Unfortunately, these existing communication systems are static in nature and are somewhat limited in what can be communicated. Accordingly, there is a need for improving communications within medical practices and clinics.

SUMMARY OF THE INVENTION

In view of the above discussion, systems, apparatus, methods, and/or computer program products that facilitate patient examinations in a medical office are provided. According to some embodiments of the present invention, a method of facilitating patient examinations in a medical office includes the following steps performed by a physician using a handheld device: identifying an examination location of a patient; identifying one or more medical procedures to be performed on a patient, wherein the one or more medical procedures are selected from the group consisting of: laboratory analysis of biological samples obtained from the patient, diagnostic tests on the patient which may include patient vaccinations and/or injections, and medical prescriptions; displaying a patient examination summary, wherein the displayed summary includes patient identification information, patient location information, patient health status information, and a list of identified medical procedures; and communicating (e.g., wirelessly, etc.) the patient examination summary to a nurse station computer within the medical office.

Embodiments of the present invention allow physicians to instruct the medical staff regarding medication (drug) samples to be taken from a pharmaceutical sample closet and given to a patient prior to discharge. A physician selects, via a handheld device, one or more drug samples to be dispensed to a patient and communicates the selected one or more drug samples to a nurse station computer. Information about samples given to patients are stored in a database for future reference and/or use with respect to drug recalls, physician sampling trends, statistical analysis, etc. Medication sampling information can also be uploaded, for example asynchronously, to a web-based server for data storage. Included in the stored medication information, but not limited thereto, are the medication name, dosage, quantity, and the medication scheduling.

Handheld devices, according to some embodiments of the present invention, may be configured to launch a third party medical prescription program and to write a pharmaceutical prescription for a patient via the third party medical prescription program. Alternatively, handheld devices according to some embodiments of the present invention may allow a physician to write a prescription and send the prescription to an external pharmacy (e.g., via fax, email, etc.).

Embodiments of the present invention allow physicians to provide patients with health-related educational information pamphlets, CDs, DVDs, etc. For example, a physician utilizes a handheld device to identify health-related educational material to be given to a patient. This information may be printed directly from the handheld device or may be communicated to a nurse station (or other) computer for delivery to the patient. In addition, identified health-related educational material may be edited by the physician via the handheld device prior to giving the material to a patient, thereby allowing a physician to customize the material for a particular patient. Accordingly, embodiments of the present invention eliminate the need to have pre-printed pamphlets which may become obsolete. Additionally, printed information may also contain the medication sampling and scheduling to be given to the patient for additional safety and compliance.

Handheld devices, according to some embodiments of the present invention, may be utilized by a physician to retrieve a patient examination summary from a nurse station computer and to allow the physician to modify the retrieved patient examination summary.

Handheld devices, according to some embodiments of the present invention, may be utilized by a physician to securely communicate directly with third party health care providers. For example, a physician may communicate with a specialist that he/she is going to refer a patient to, etc.

Handheld devices, according to some embodiments of the present invention, may be configured to receive advertisements from external third parties and to display received advertisements. For example, a pharmaceutical company may send advertisements to a physician's handheld device for display thereon.

Handheld devices, according to some embodiments of the present invention, may be configured to display third party referral forms, each form associated with a respective specialist to whom a physician wishes to refer a patient to. For example, a physician can display and fill out a referral form for a cardiologist to whom the physician is referring a patient.

Handheld devices, according to some embodiments of the present invention, may be configured to record and store dictation by a physician. Handheld devices, according to some embodiments of the present invention, may be configured to send and receive voice and/or text communications with other device within a medical office. Moreover, a handheld device may be configured to send and receive electronic mail.

According to some embodiments of the present invention, a medical office system that facilitates patient examinations, includes a nurse station computer; and one or more handheld devices, wherein each handheld device communicates wirelessly with the nurse station computer. Each handheld device is configured to identify an examination location of a patient, to identify one or more procedures to be performed on the patient, to display a patient examination summary, wherein the displayed summary includes patient identification information, patient location information, patient health status information, and a list of identified procedures to be performed on the patient, and to communicate the patient examination summary wirelessly to the nurse station computer.

According to some embodiments of the present invention, a nurse station computer receives a patient examination summary from a handheld device, and displays all of the information in the patient examination summary in a single GUI displayed on a screen thereof. Within the single GUI is displayed, in a compartmentalized manner, patient identification information, patient location information, patient health status information, information about one or more medical procedures to be performed, information about one or more drug samples to be dispensed to a patient, information about one or more pharmaceutical prescriptions for a patient, and/or information about health-related educational material to be given to a patient.

According to some embodiments of the present invention, the medical office system includes a patient reception station computer that receives and stores patient demographic information, and that is configured to communicate wirelessly with the nurse station computer and with each handheld device. The reception station computer is configured to add patients checking in at the medical office to a physician's daily log that is displayed on the physician's handheld device.

Embodiments of the present invention allow physicians and their respective staff to initiate a "Code Blue" for emergency purposes from anywhere within a medical office. The Code Blue, once initialized, can be seen on any computer or handheld device in the medical office. The Code Blue automatically designates the location of the emergency to staff members, thus saving critical time for response. An audio alert may be sounded by each handheld device in response to receiving emergency information transmitted by another handheld device or by the nurse station computer (or by any other medical office system device).

Embodiments of the present invention allow physicians to request lab tests and services at the point of care and transmit these requests wirelessly to a diagnostic lab client server or web-based communication portal. For example, each handheld device and nurse station computer may be configured to communicate directly with a third party laboratory service and request medical laboratory work directly therefrom.

Embodiments of the present invention facilitate better communications and more dynamic communications between a physician and his/her medical staff. Embodiments of the present invention can eliminate the need for face-to-face communications between physicians and medical staff that is traditionally required when communicating regarding procedural tests and patient referrals. Moreover, embodiments of the present invention can run independently of an office management system and serve as a front office and back-end clinical organizational work flow tool.

Embodiments of the present invention may be advantageous because they serve to aid the physician and his/her medical staff by utilizing their collective time more efficiently, and therefore can afford the medical office the ability to see sick patients in a more timely fashion. This ultimately can result in greater income for the medical office, and likewise can allow patients to be seen sooner, rather than later. In more rural areas of the country where there are fewer physicians, embodiments of the present invention can enhance patient workflow and, thereby, allow physicians to better serve their communities.

BRIEF DESCRIPTION OF THE DRAWINGS

FIGS. 14-16 illustrate various GUIs that are displayed within a reception station computer, according to some embodiments of the present invention.

DETAILED DESCRIPTION OF EMBODIMENTS OF THE INVENTION

Figure 1:
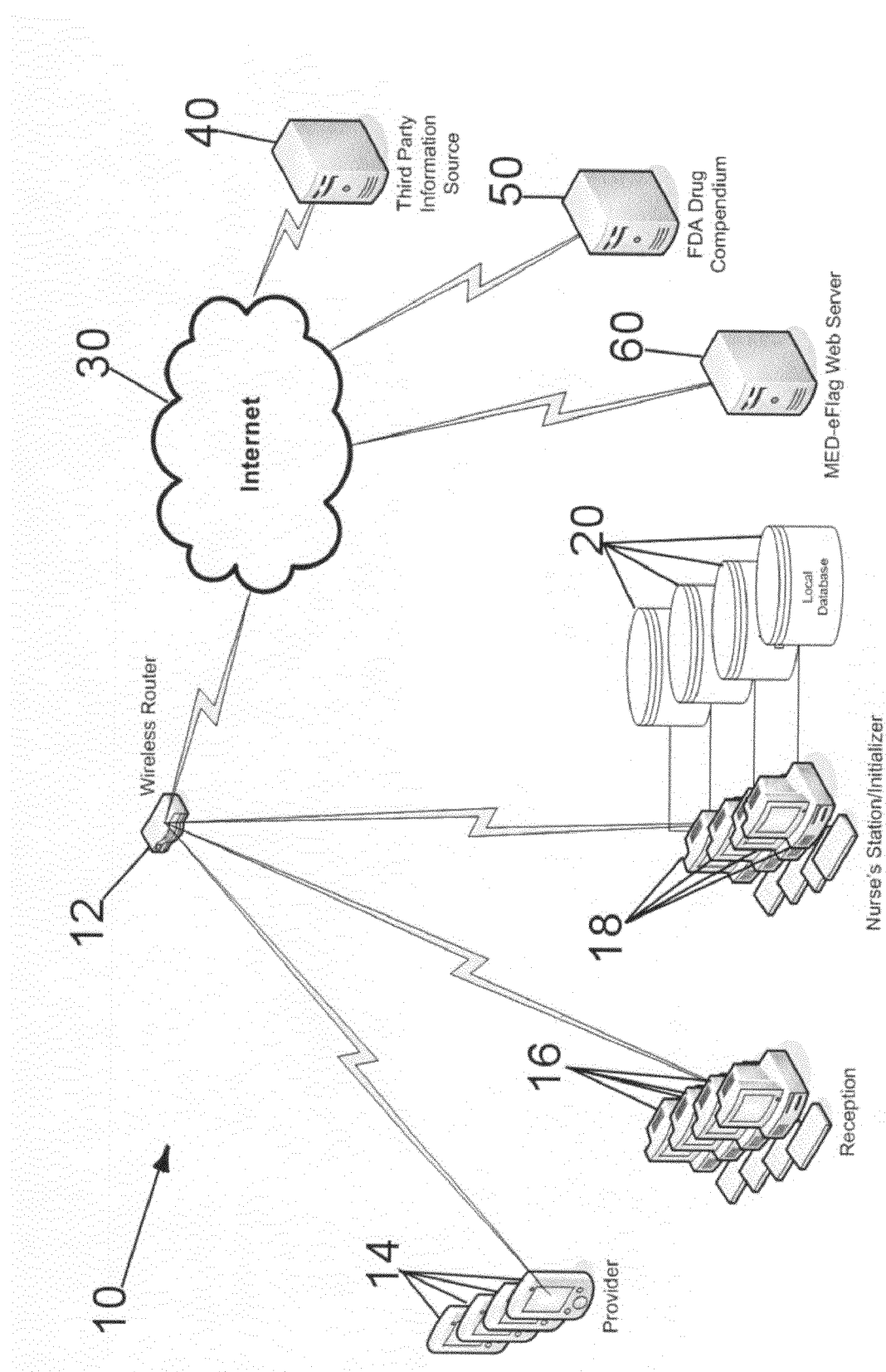
FIG. 1 illustrates a wireless communications network for use by a medical office for implementing various aspects of embodiments of the present invention.

The present invention now will be described more fully hereinafter with reference to the accompanying drawings, in which illustrated embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items. As used herein, the term "consisting of" followed by a list of features, integers, steps, operations, elements, components, and/or groups includes one or more of the features, integers, steps, operations, elements, components, and/or groups thereof.

As will be appreciated by one of skill in the art, the present invention can be embodied as graphical user interfaces for handheld devices, as well as methods, computer program products, and data processing systems for facilitating patient examination in a medical office. Accordingly, the present invention can take the form of an entirely hardware embodiment, an entirely software (including firmware, resident software, micro-code, etc.) embodiment, or an embodiment containing both software and hardware aspects. Embodiments of the present invention can take the form of computer program products on computer-usable or computer-readable storage medium having computer-usable or computer-readable program code means embodied in the medium for use by or in connection with an instruction execution system. In the context of this document, a computer-usable or computer-readable medium can be any means that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of the present invention may be written in object oriented programming languages (e.g., JAVA®, Smalltalk or C++) and/or may also be written in conventional procedural programming languages (e.g., "C"). However, embodiments of the present invention do not depend on implementation with a particular programming language.

The present invention is described herein with reference to flowchart and/or block diagram illustrations of systems, apparatus, methods, and/or computer program products in accordance with exemplary embodiments of the invention. It will be understood that each block of the flowchart and/or block diagram illustrations, and combinations of blocks in the flowchart and/or block diagram illustrations, may be implemented by computer program instructions and/or hardware operations. These computer program instructions may be provided to a processor of a general purpose computer, a special purpose computer, or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer usable or computer-readable memory that may direct a computing device (such as a handheld device, a computer or other programmable data processing apparatus) to function in a particular manner, such that the instructions stored in the computer usable or computer-readable memory produce an article of manufacture including instructions that implement the function specified in the flowchart and/or block diagram block or blocks.

The computer program instructions may also be loaded onto a handheld device, a computer or other programmable data processing apparatus to cause a series of operational steps to be performed on the computer or other programmable apparatus to produce a computer implemented process such that the instructions that execute on the handheld device, computer or other programmable apparatus provide steps for implementing the functions specified in the flowchart and/or block diagram block or blocks.

It should be noted that, in some embodiments of the present invention, the functions noted in the flowchart blocks may occur out of the order noted in the figures. For example, two blocks shown in succession may in fact be executed substantially concurrently or the blocks may sometimes be executed in reverse order, depending on the functionality involved. Furthermore, in certain embodiments of the present invention, such as object oriented programming embodiments, the sequential nature of the flowcharts may be replaced with an object model such that operations and/or functions may be performed in parallel or sequentially.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "physician" is intended to include any and all health care providers (e.g., practitioners, optometrists, ophthalmologists, etc.), without limitation.

As used herein, the term "medical office" is intended to include all facilities where patients are examined and/or treated by health care providers, without limitation.

FIG. 1 illustrates an "eFlag" network 10 for use within a medical office according to some embodiments of the present invention. Each device connected to an eFlag network 10 executes the eFlag software application that implements the various functions and displays the various graphical user interfaces (GUIs) described hereinbelow. Using the eFlag software application, different physicians in a medical office can each simultaneously utilize his/her own handheld device 14 and transmit to any networked device in the medical office (i.e., reception station computers 16, nurse station computers 18, and other devices executing the eFlag software application that are connected to the network 10). Therefore, each physician can independently communicate with either the same nursing staff member, or individual staff members at different locations.

The illustrated eFlag network 10 includes a wireless router 12, a plurality of handheld devices 14, one or more reception station computers 16, and one or more nurse station computers 18. Each nurse station computer 18 may include data storage capabilities such as, for example, a database 20. In the illustrated embodiment, wireless router 12 is configured to communicate with various third parties via the Internet 30 or other communications networks. For example, information may be sought from one or more third party information sources 40 (e.g., drug information may be sought from a web site hosting the Food and Drug Administration compendium 50). A server 60 may exist outside of a medical office that contains various software applications for implementing embodiments of the present invention. Thus, software for implementing embodiments of the present invention may execute on individual handheld devices 14, on reception station computers 16, on nurse station computers 18, on an external web server 60, and/or on some combination of the above.

Web server 60 is configured to provide updates to the eFlag software application executing on devices in a medical office. According to some embodiments of the present invention, updates, patches, etc. can be automatically downloaded, and/or periodically downloaded from the web server 60 to a handheld device 14, reception station computer 16 and/or nurse station computer 18.

Handheld devices 14 according to embodiments of the present invention are typically small enough to be held by one hand and typically include such features as handwriting recognition, pop-up keypads and number pads, communication software for Internet access, and the ability to hook up to a docking station to exchange information therewith. Handheld devices 14, according to embodiments of the present invention, are intended to be easily and unobtrusively carried with a physician as he/she moves from exam room to exam room. Immediately after a physician has seen a patient at the point of care, information indicating the necessary testing to be performed, including diagnostic studies, lab tests, medication samples, prescriptions etc., is transmitted wirelessly from a handheld device 14 to a nurse station computer 18.

As used herein, the term "handheld device" is intended to include, but is not limited to, PDAs, radiotelephones, web-enabled radiotelephones, and other mobile/wireless devices. Exemplary handheld devices which may be utilized in accordance with embodiments of the present invention include, but are not limited to, devices available from Handspring, Inc., Mountain View, Calif.; Palm, Inc., Santa Clara, Calif.; Compaq Computer Corporation, Houston, Tex.; Hewlett-Packard Company, Palo Alto, Calif.; IBM, Armonk, N.Y.; HandEra, Inc., Des Moines, Iowa; Psion PLC, London, UK; Nokia Corporation, Keilalahdentie, Finland; Ericsson, Inc., New York, N.Y.; and Motorola, Inc., Schaumburg, Ill.

Embodiments of an eFlag network can work independently of any office management system and do not require integration or interfacing. The eFlag network will work on any desktop computer-based platform, whether it is Windows®, Apple®, Linux, or others. The eFlag network will work on any handheld device platform including, but not limited to, Windows-CE, Palm Pilot, Blackberry, Nokia, etc.

Each handheld device 14 allows a respective physician to communicate wirelessly with a nurse station computer 18 as to the status of a patient once the physician has completed examination (and/or during examination) of the patient. Via a handheld device 14, a physician can notify a nurse that a patient is ready to check out, that a patient should be held in the examination room after diagnostic studies for further discussion, that the patient needs to schedule one or more diagnostic procedures, that the patient must see the office manager prior to discharge, that x-rays are needed, etc.

The eFlag software application executing on a nurse station computer 18 allows a nurse to communicate wirelessly back to a physician's handheld device 14 regarding specific things such as: incoming telephone calls from other physicians, prescription refill requests, and questions pertinent to patients. Moreover, physicians can be notified as to a patient's readiness to begin certain procedures.

The eFlag software application executing on a reception station computer 16 allows the medical office reception desk to notify the nursing staff when a patient is checked in and ready to be brought to an examination room. The reception station computer 16 can also send a message to the nurse station computer 18 regarding pharmaceutical representatives waiting to be seen for drug detailing and signature, patients requiring vaccinations, etc.

As used throughout, the terms "user activation" and "activation" with respect to a GUI control in a GUI shall include user "touching" (e.g., via a finger, stylus, etc.) of the GUI control, which causes the GUI control to perform one or more functions.

Embodiments of the eFlag software application allow a physician to undergo a step-by-step initialization process wherein each of the displayed GUI controls within the various GUIs described herein can be configured with nomenclature that best fits the physician's own practice setting. Therefore, embodiments of the present invention provide a fully customizable system that can be utilized in a medical office setting, whether that particular office happens to be internal medicine, cardiology, gastroenterology, pulmonary medicine, etc. It may even be implemented and utilized in other health fields such as dentistry, optometry, podiatry, etc.

Embodiments of the eFlag software application allow physicians to communicate wirelessly via a handheld device 14 using audio and/or text to a nurse station computer 18, and to other eFlag network devices, with multi-directional capability without the need for web e-mail, practice management text messaging systems, etc. Moreover, the present invention also allows audio and/or text communications in the same multi-directional manner with any handheld device or computing device utilizing the eFlag software application.

FIGS. 2-9 and 10A-10B illustrate various GUIs displayed within a handheld device 14 executing the eFlag software application, according to some embodiments of the present invention. The illustrated GUIs are exemplary only and embodiments of the present invention are not limited to these exact GUIs. These illustrated GUIs serve to explain some embodiments of the present invention from the point of view of a physician holding a handheld device at the point of care (i.e., during examination of a patient). All of the illustrated GUIs and GUI controls and other displayed information illustrated in the figures can be customized with nomenclature that best represents the medical field in which it is being utilized.

Figure 2:
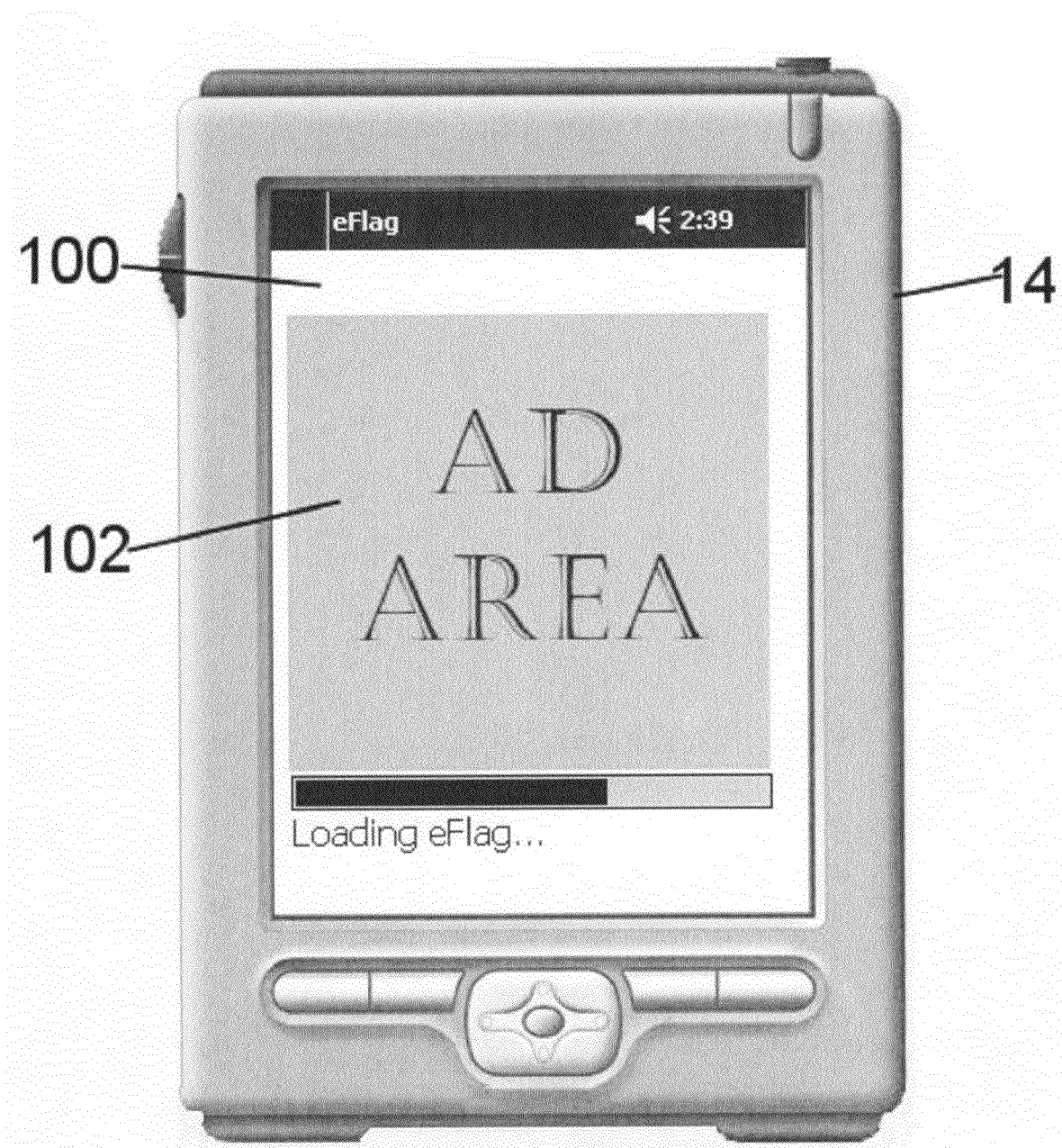
FIGS. 2-9 and 10A-10B illustrate various graphical user interfaces (GUIs) that are displayed via handheld communications devices, according to some embodiments of the present invention.

FIG. 2 illustrates an initial GUI 100 that a physician will see when the eFlag software application is initiated on a handheld device 14. As the eFlag software application is loading, an area 102 in GUI 100 is available for displaying various information to the physician. Examples of such information may include, but is not limited to; vaccine ordering reminders, drug recalls, pharmaceutical medication information and dosaging information, advertisements, and/or alerts regarding upcoming versions or updates to the eFlag software application.

Figure 3:
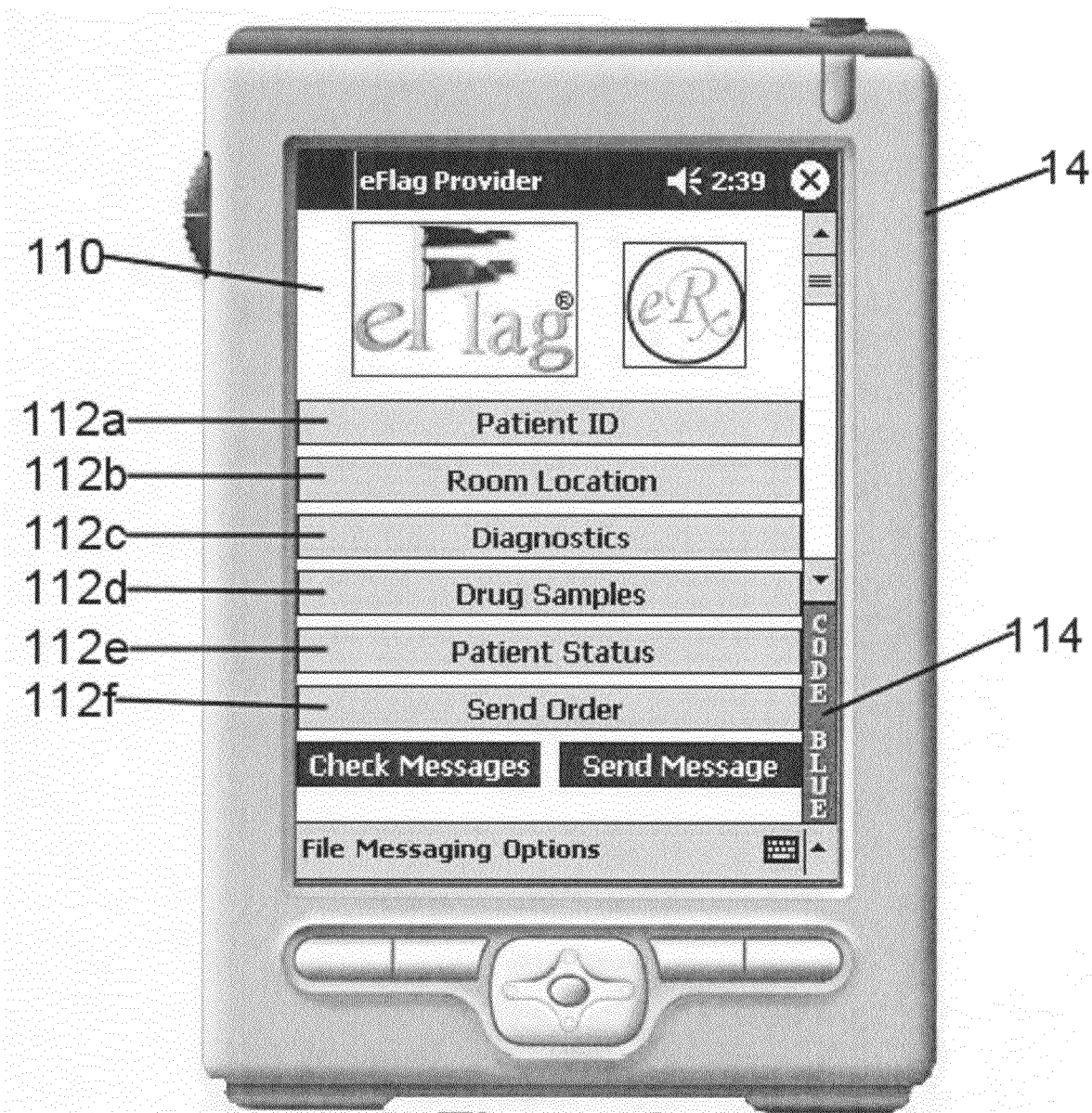
Figure 4:
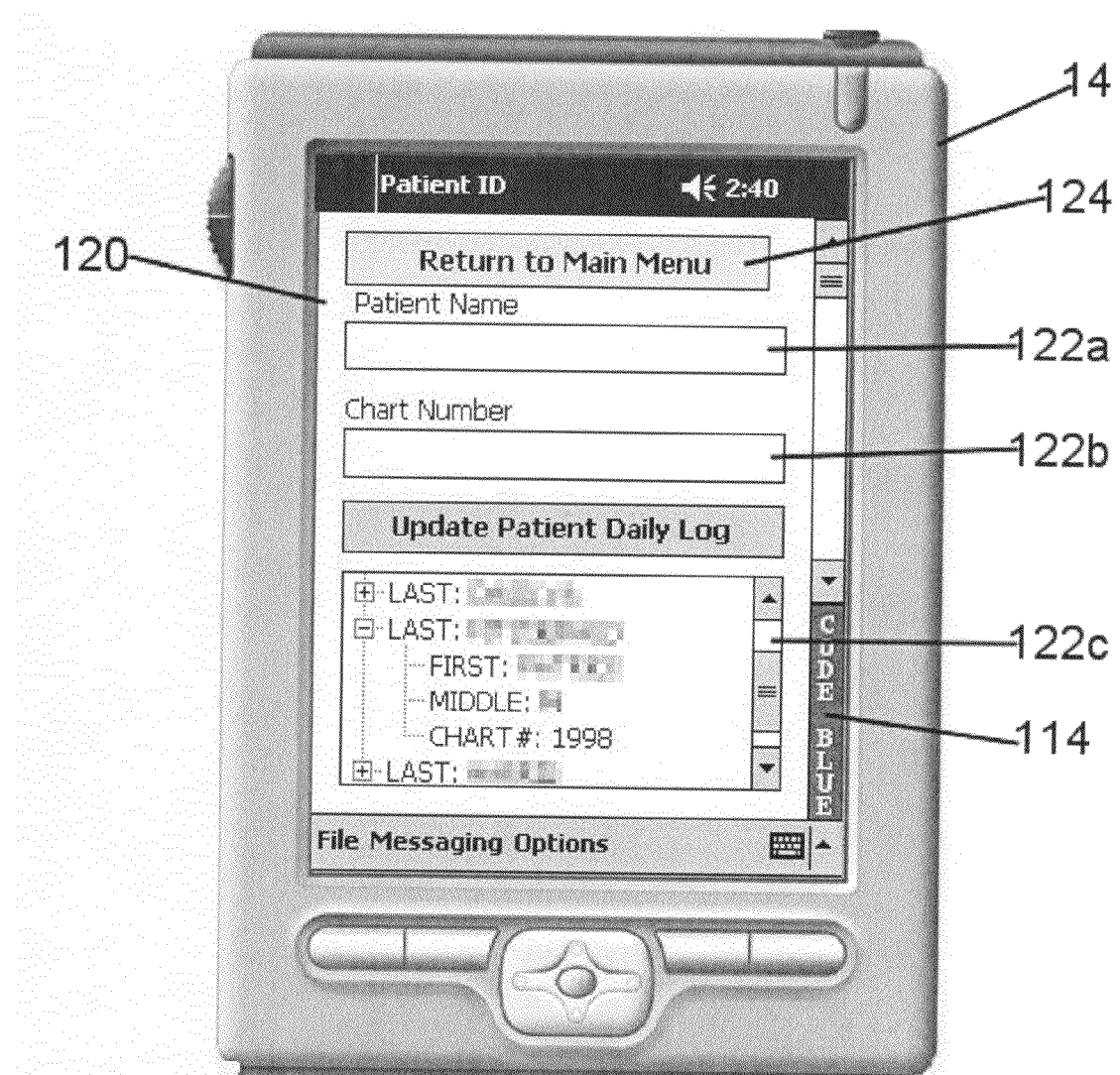

Once the eFlag software application is loaded, the GUI 110 illustrated in FIG. 3 is displayed. The illustrated GUI 110 includes a plurality of GUI controls, each of which is configured to perform one or more functions when activated (i.e., touched) by a user. GUI control 112a, entitled "Patient ID", is configured to display GUI 120, illustrated in FIG. 4. GUI 120 displays the daily log of patients to be examined. The illustrated GUI 120 includes a text box 122a for inputting/displaying a patient's name, a text box 122b for inputting/displaying a chart number assigned to a patient, and a daily log 122c of patient names added from the reception station computer 16, or from another source. A physician can scroll down the list of patient names in the daily log 122c and click on a patient name to bring up the patient's name and chart number in GUI controls 122a, 122b, respectively. The daily log 122c makes it less time consuming than having the physician type in the name and chart numbers with each patient visit. However, if a patient name is not found in the daily log 122c, or if the physician so chooses, a mini-keyboard can be called up and displayed within the GUI 120 that allows free text (i.e., a patient name and chart number) to be entered into GUI controls 122a, 122b. GUI 120 also includes GUI control 114, entitled "Code Blue" (described in detail below) and GUI control 124, entitled "Return to Main Menu", that, when activated, returns the user to GUI 110 (FIG. 3).

Figure 5:
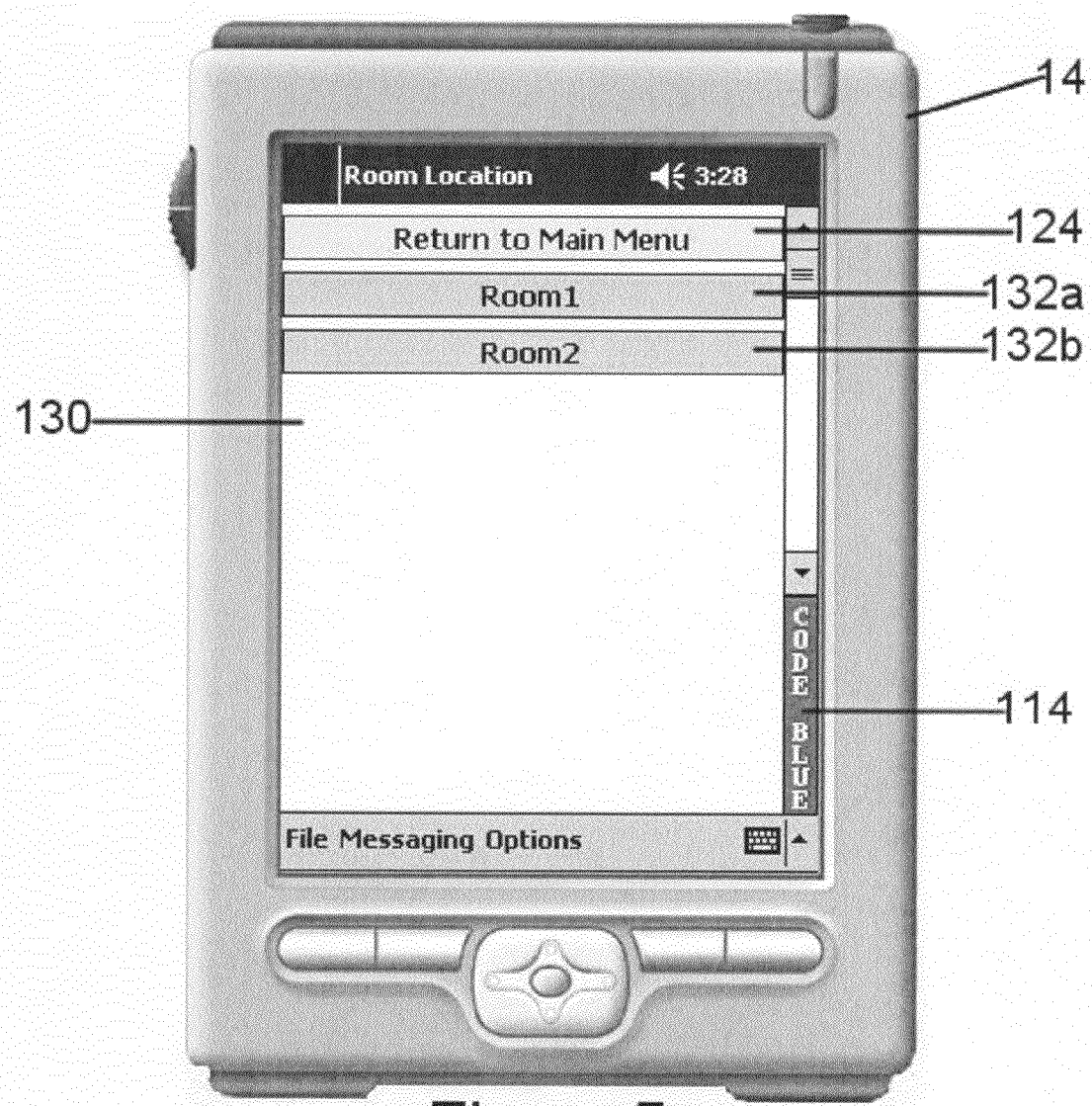

Still referring to FIG. 3, GUI control 112b, entitled "Room Location", is configured to display GUI 130, illustrated in FIG. 5. GUI 130 includes a plurality of GUI controls, each labeled with a room number, and from which a physician selects the room having the patient that he/she is about to examine. For example, GUI control 132a, entitled "Room1", is selected by the physician if the patient about to be examined is in Room 1. GUI control 132b, entitled "Room2", is selected by the physician if the patient about to be examined is in Room 2. GUI 130 also includes GUI control 114, entitled "Code Blue" (described in detail below) and GUI control 124, entitled "Return to Main Menu", that, when activated, returns the user to GUI 110 (FIG. 3).

Initially, upon seeing a patient, a physician activates GUI control 112b (Room Location) which causes GUI 130 (FIG. 5) to be displayed. According to embodiments of the present invention, a patient is identified firsthand by his/her physical location within a medical office. The various GUI controls (e.g., 132a, 132b) may utilize nomenclature that is customized to indicate each of the examination rooms or other areas within a medical office such as a procedure room, radiology room, eye examination room, etc. An area/room must be selected by the physician by activating one of the GUI controls in GUI 130 (i.e., 132a, 132b) in order to notify the nurse of the location of a patient. The eFlag software application will not allow any information entered into the handheld device 14 to be transmitted to a nurse station computer 18 until this step is completed to ensure that tasks are performed on the correct patient.

Figure 6A:
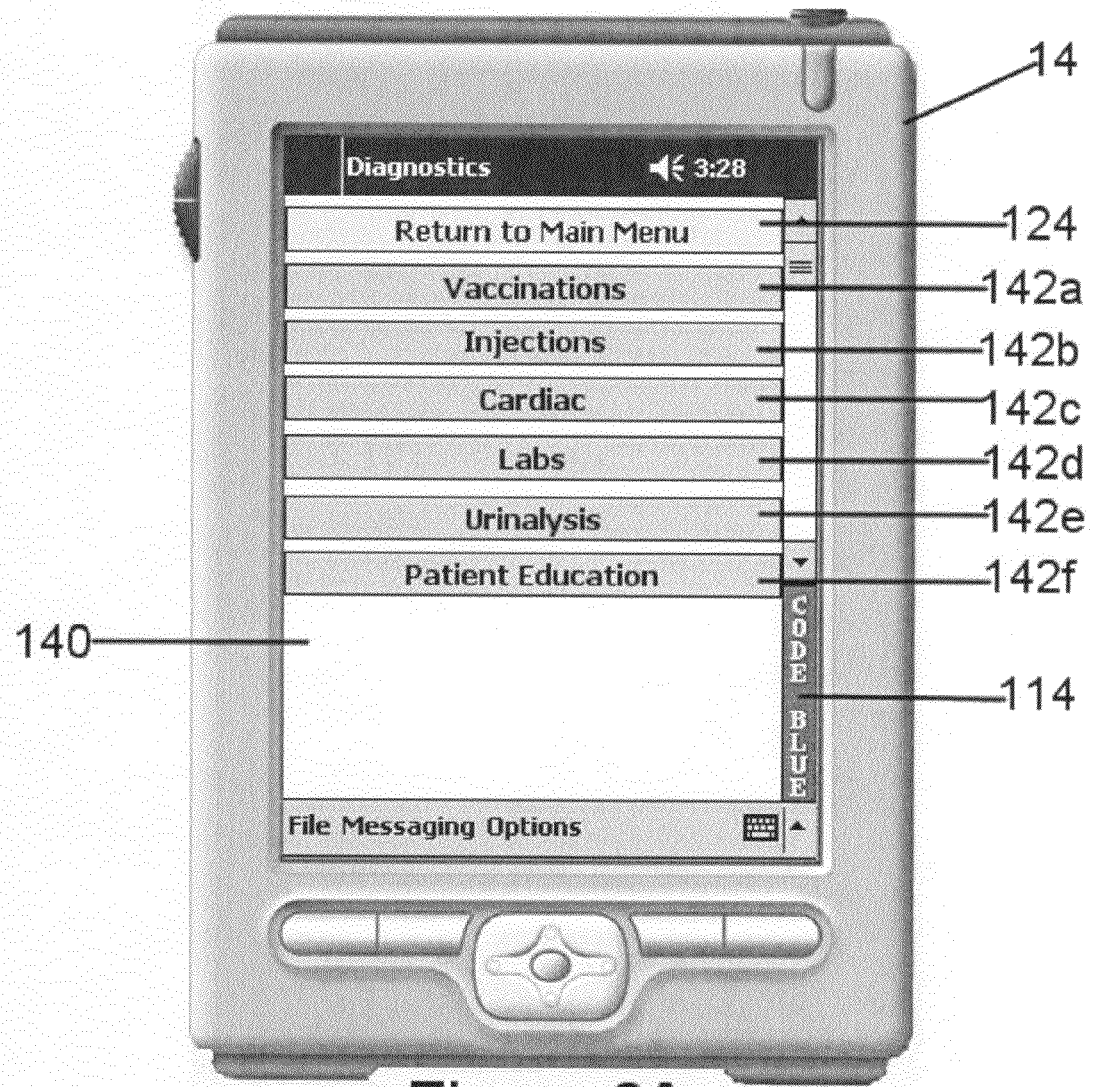
Figure 6B:
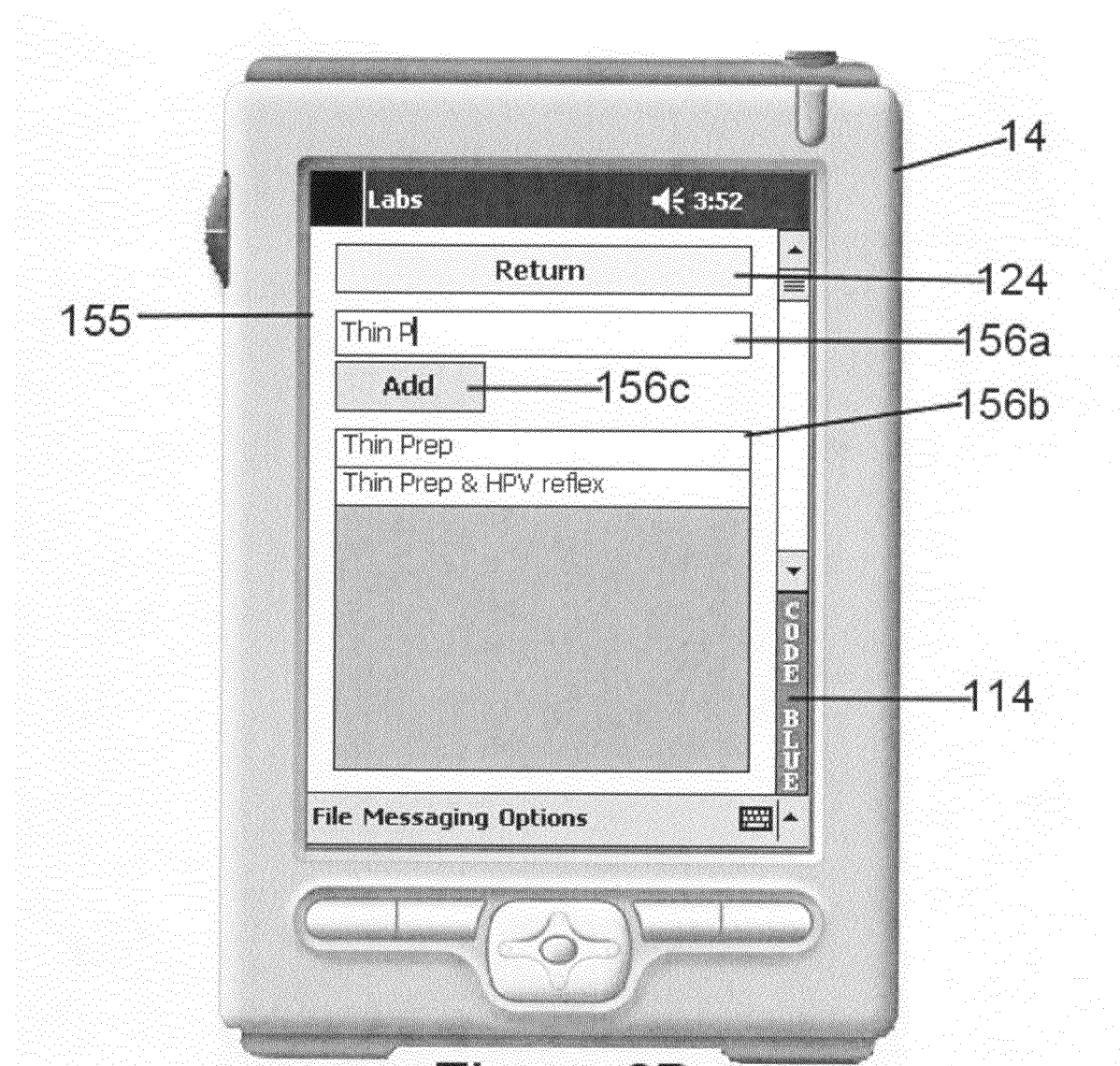

Referring back to FIG. 3, GUI control 112c, entitled "Diagnostics", is configured to display GUI 140, illustrated in FIG. 6A. GUI 140 includes a plurality of GUI controls, each labeled with a type of diagnostic test/procedure, and from which a physician selects tests and procedures to be performed on a patient. For example, GUI control 142a, entitled "Vaccinations", is selected by a physician if a patient should receive one or more vaccinations. For example, activation of GUI control 142a is configured to display another GUI (not shown) from which the physician can select one or more vaccinations (e.g., influenza, pneumonia, hepatitis B, tetanus, tuberculin, etc.) to be administered to a patient. Similarly, activation of GUI control 142b is configured to display another GUI (not shown) from which the physician can select one or more injections (e.g., steroids, etc.) to be administered to a patient.

GUI control 142c, entitled "Cardiac", is selected by the physician if the patient should undergo cardiac-related tests and procedures. When activated, GUI control 142c is configured to display GUI 150, illustrated in FIG. 7. GUI 150 includes a plurality of GUI controls, each labeled with a type of cardiac test or procedure. For example, GUI control 152a, entitled "EKG", is activated by the physician if the patient is to undergo an EKG test. GUI control 152b, entitled "Rhythm Strip", is activated by the physician if the patient is to undergo a heart rhythm test. GUI control 152c, entitled "Cardiac Monitor", is activated by the physician if the patient is to be connected to a heart monitor and undergo one or more heart-related tests. GUI control 152d, entitled "Treadmill Test", is activated by the physician if the patient is to undergo a treadmill stress test. GUI 150 also includes GUI control 114, entitled "Code Blue" (described in detail below) and GUI control 124, entitled "Return to Main Menu", that, when activated, returns the user to GUI 110 (FIG. 3). Once the physician selects one or more diagnostic tests and/or procedures to be performed on the patient, GUI control 124 is activated to return to GUI 110.

Depending on the specialty of the physician, the various GUI controls displayed in GUI 140 (as well as GUI 150 and any other Diagnostic-related GUIs) can be individualized according to that specialty. GUI controls illustrated herein are representative of the more commonly used functions in an internal medicine medical office, and are intended to be examples only. If the medical office implementing the eFlag network 10 (FIG. 1) is an Optometrist's office, embodiments of GUI 140 and 150, for example, would be customized to the practice of optometry. For example, an optometrist would use drop down menus and other GUI controls to choose numerical values indicating prescription strength eyeglasses, etc. These eyeglass prescriptions can be forwarded to other areas within the office, printed, or sent via email to other providers such as Ophthalmologists. These same eyeglass prescriptions can also be saved in a database for future retrieval, etc.

Diagnostic-related GUI controls may be static or dynamic. For example, upon activating GUI control 142a (Vaccinations) in GUI 140, a drop down menu box with a pre-selected list of vaccinations may be displayed that allows a physician to select/check the particular vaccination to be given to a patient. Alternatively, a text input GUI control may be displayed that allows a physician to manually enter, for example via a pop-up miniature keyboard, particular vaccinations to be given. This dynamic function is an innate function of the eFlag software application and offers a physician a wider array of options. In addition, the Diagnostic-related GUIs of embodiments of the present invention are capable of interfacing with any third party diagnostic laboratory software in order to pass laboratory requests/orders directly into a third party laboratory system.

The number of GUI controls in GUIs 140 and 150 (as well as any other GUI described herein) may vary by physician in a medical office. If so chosen, after one physician within the same medical office and specialty establishes all the choices for the GUI controls in GUIs 140 and 150, the remaining physicians in the medical office have the option of using the same nomenclature into their own handheld device 14 or using a different nomenclature. This allows for time saving and quicker deployment of the program into many medical offices.

Figure 6C:
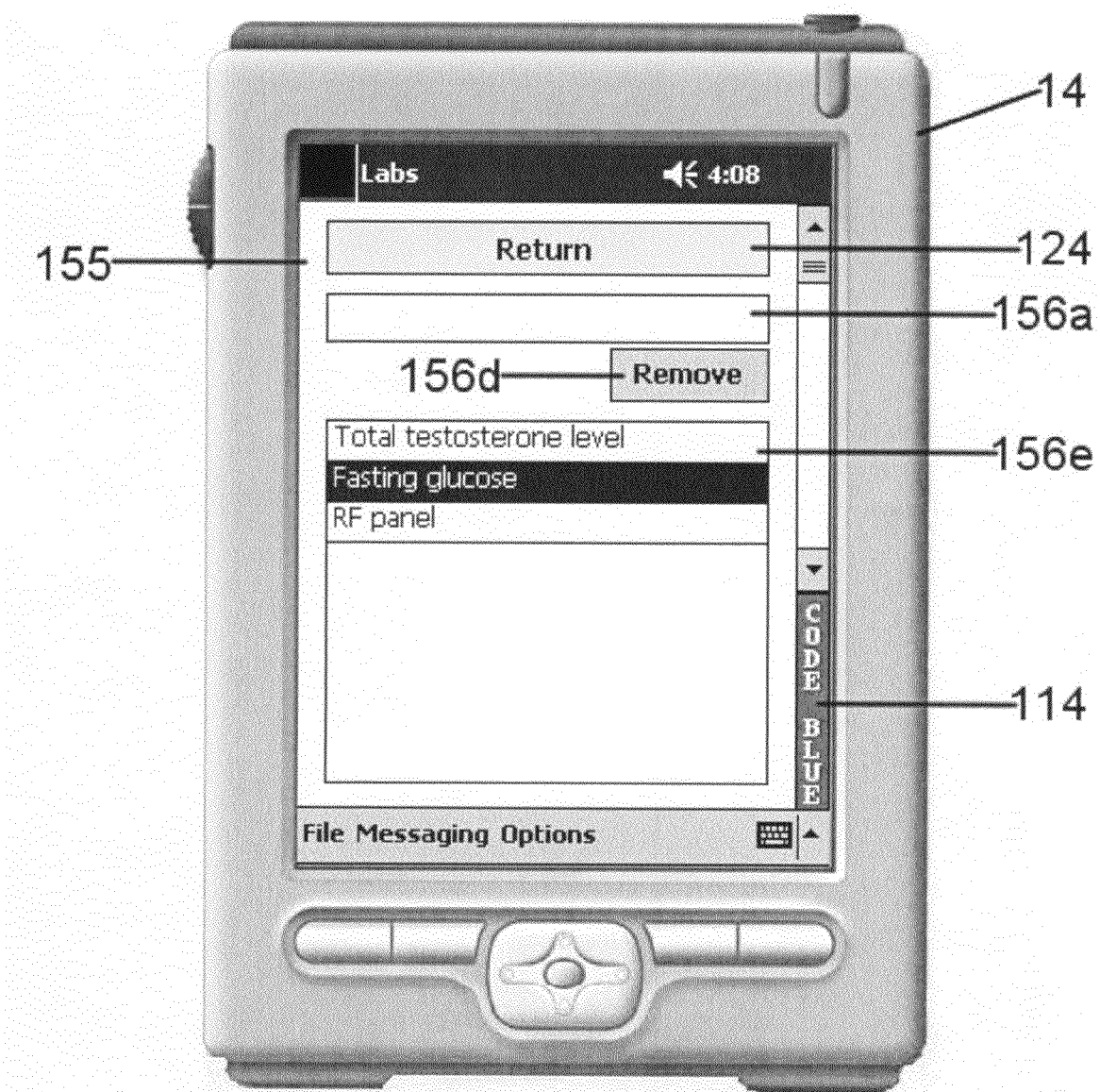
Figure 7:
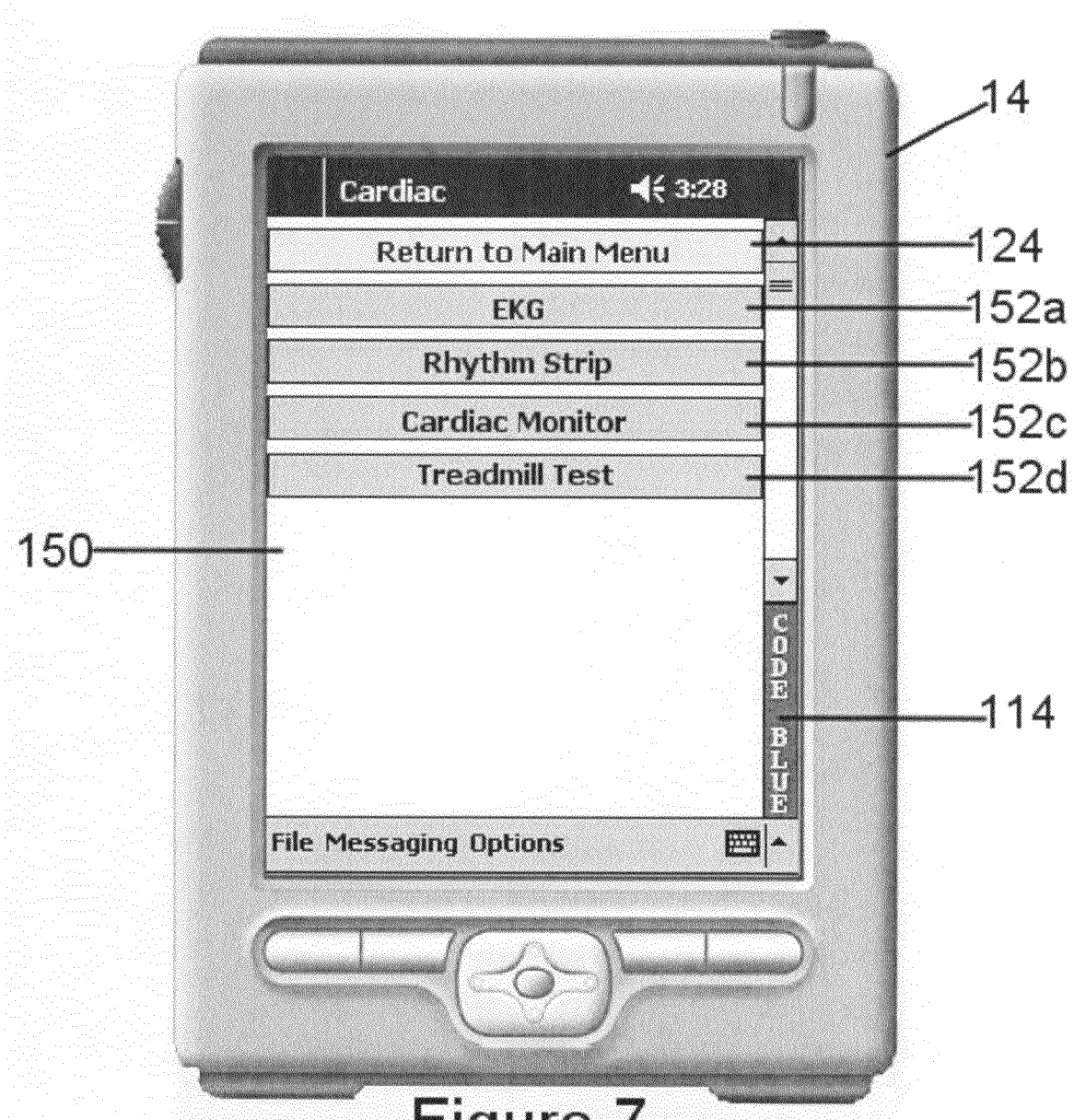

Referring back to FIG. 6A, GUI control 142d, entitled "Labs", is selected by a physician if a patient should undergo certain lab tests (e.g., blood tests, etc.) Activation of GUI control 142d is configured to display another GUI 155, FIG. 6B, from which the physician can select lab tests. According to some embodiments of the present invention, this function is intended to by dynamic in that an auto-scroll function of each lab test is provided. For example, a physician types the first letters of a desired lab test in text box 156a, and all listed labs beginning with these letters will appear within a list box 156b. The selected lab test is highlighted by touching the screen over the desired lab test, and then touching an Add button 156c, for example. A selected lab test appears in list box 156e (FIG. 6C) and indicates that it is a chosen item for that patient. As each desired lab test is added, the names appear within the lab order list box 156b for the physician to see and verify before returning to the main screen (i.e., GUI 110, FIG. 3). If a lab test is to be removed from lab order list box 156e, the lab test is highlighted, and selecting the remove button 156d will delete that lab test from the list box, as illustrated in FIG. 6C.

GUI control 142e, entitled "Urinalysis", is selected by a physician if a patient should undergo a urinalysis test. GUI control 142f, entitled "Patient Education", is selected by a physician if a patient should be provided some sort of health-related information. For example, a patient may be given health-related educational material prior to leaving the medical office. According to some embodiments of the present invention, upon activation, GUI control 142f may be configured to display a list of educational handouts pertinent to the patient care and from which a physician can select to give to a patient. The handouts can be preprinted or can be printed on-demand. Moreover, handouts can be customized and edited by a physician. Examples of this include, but are not limited to, diabetic instructions on finger-stick glucose testing, monitoring blood pressures at home, use of inhalers for asthmatics, dietary or calorie count sheets, etc. According to some embodiments of the present invention, this function is intended to by dynamic in that an auto-scroll function of various topics can be provided. For example, a physician types the first letters of a desired topic, and all listed topics beginning with these letters will appear within a list box. The physician will highlight a handout associated with a topic and add to a list box. Once the order is sent to the nurse station computer 18, a category box will be displayed showing the handout chosen, and it can then be printed and given to the patient.

GUI 140 also includes GUI control 114, entitled "Code Blue" (described in detail below) and GUI control 124, entitled "Return to Main Menu", that, when activated, returns the user to GUI 110 (FIG. 3).

Thus, during the examination of a patient, a physician will systematically activate various GUI controls in GUIs 140 and 150 in order to request certain tests and procedures to be performed on a patient. The amount of time it would take to go through a cycle of an examination depends on the number of diagnostic studies/tests to be ordered on a particular patient at the point of care. However, it may, for example, only take an average of 6-12 seconds to complete one task order cycle (i.e., to order procedures/tests for a patient).

Figure 8:
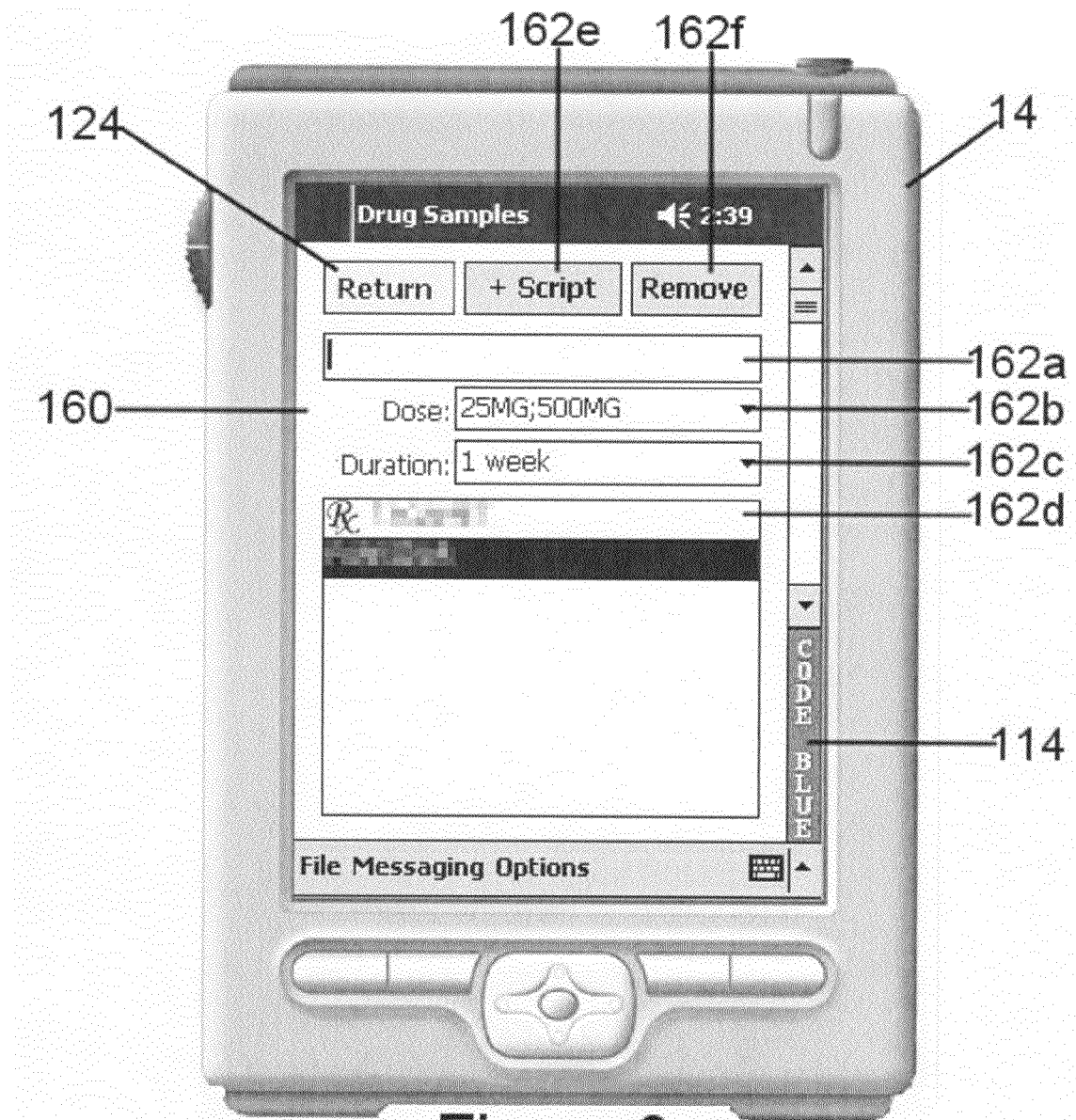

Referring back to FIG. 3, GUI control 112d, entitled "Drug Samples", is configured to display GUI 160, illustrated in FIG. 8. GUI 160 includes a plurality of GUI controls associated with drug samples to be given to patients. For example, GUI control 162a is a text box for inputting a medication sample to be provided to a patient. Using GUI control 162a, a physician can selectively choose from a database 20 of pharmaceutical medications by entering the first characters of the drug name in GUI control 162a. As the characters are typed in manually, the list of medication names will begin to appear in the list box 162d. Once the correct medicine is found and highlighted, it will be automatically placed into GUI control 162a with the corresponding dosages. Alternatively, a physician can type in the name of a medication if not in the database, and can select the dosage and duration via GUI controls 162b, 162c, respectively.

A physician uses GUI control 162b to select the appropriate dosage, and GUI control 162c to select the duration for which he/she wishes to provide samples to the patient. If the physician is planning on sending a prescription along with the same sample medication, then GUI control 162e, entitled "+script", can be activated which will place an "Rx" icon to the left of the medicine name in the list box 162d. Conversely, this "Rx" icon can be removed with GUI control entitled "−script" (not shown). Additionally, GUI control 162f, when activated, removes entries from the various GUI controls in GUI 160.

According to embodiments of the present invention, several options exist in establishing a drug sample database 20 and respective doses upon initialization of the eFlag software application in a respective medical office. One example is creating a list of the most commonly used medications which can be downloaded from a third party information source (e.g., 40, FIG. 1) during the setup process upon initial installation of the eFlag software application. Another example is having the present invention update the sample medications on a scheduled cycle by updating from a web-based database (i.e., from a third party information source 40, FIG. 1) and loading into the eFlag software application. Once again, this is an example of a dynamic capability in which there are choices of either choosing a medication, the name of which is stored in the database, or typing in a specific drug sample using a pop-up keyboard.

GUI 160 also includes GUI control 114, entitled "Code Blue" (described in detail below) and GUI control 124, entitled "Return to Main Menu", that, when activated, returns the user to GUI 110 (FIG. 3).

Figure 9:
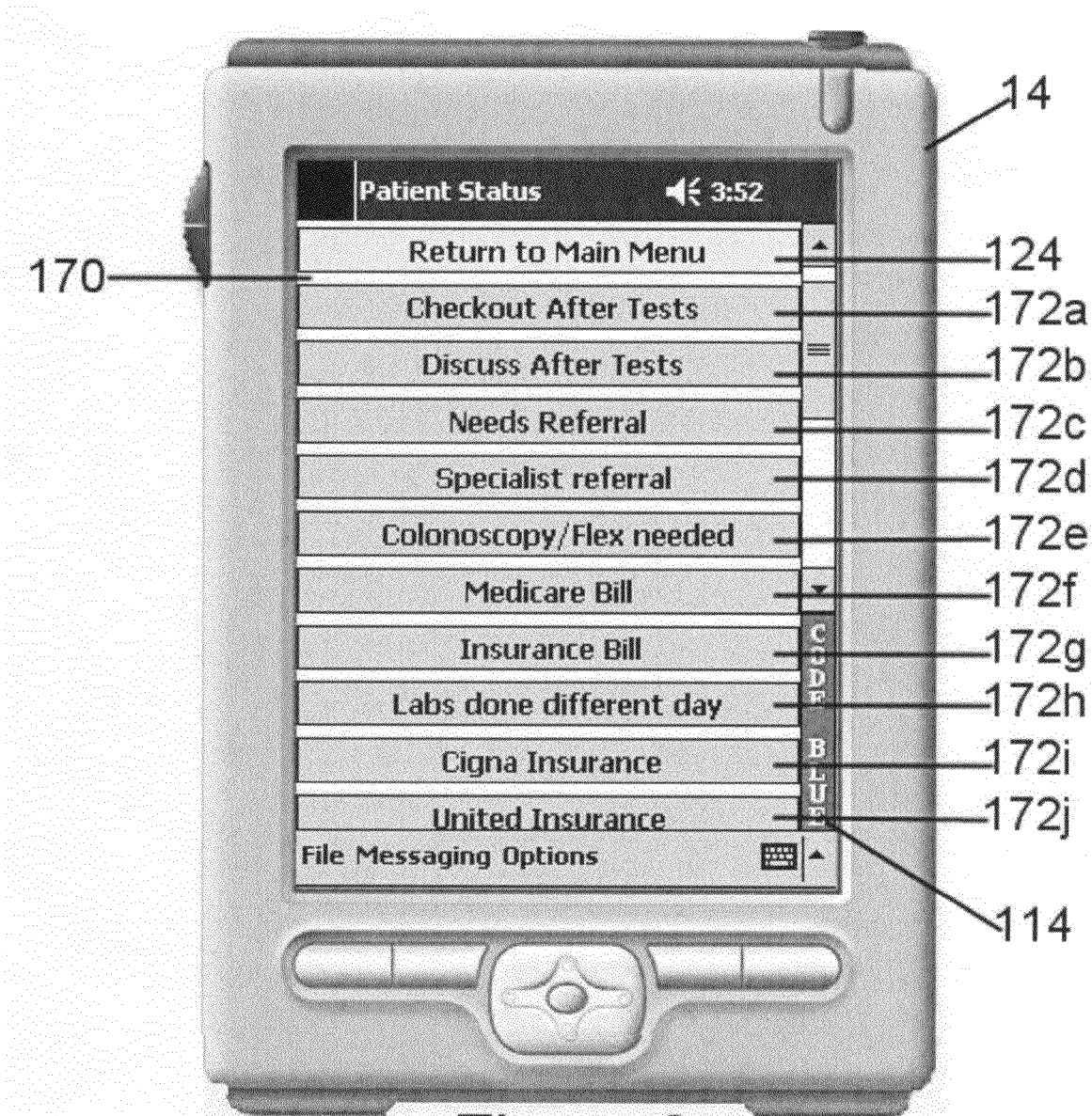

Referring back to FIG. 3, GUI control 112e, entitled "Patient Status", is configured to display GUI 170, illustrated in FIG. 9. The Patient Status GUI 170 displays a plurality of static indicators of the disposition of a patient once the physician has finished the examination of the patient and is ready to leave the room to see another patient. GUI 170 confirms that the nursing staff has received the various communications from the physician relating to any tests/procedures, vaccinations, referrals, etc.

The illustrated GUI 170 includes a plurality of static indicators 172a-172j associated with the status of a particular patient. Each of these indicators can be customizable to a practitioner's own nomenclature, and embodiments of the present invention are not limited to the displayed indicators 172a-172j. In the illustrated GUI 170, indicator 172a, entitled "Checkout After Tests", indicates that the patient can be checked out upon a nurse's completion of the ordered tests by the physician. Indicator 172b, entitled "Discuss after Tests", indicates that the nurse is to leave the patient in the room for further discussion by the physician after the tests are completed. Indicator 172c, entitled "Needs Referral", indicates that a general referral for the patient is needed. Indicator 172d, entitled "Specialist Referral", indicates the patient needs a specialist's referral upon checkout, and that a referral may have been printed (or may need to be printed) and/or sent to the referral physician. Indicator 172e, entitled "Colonoscopy/Flex needed", indicates that the patient needs a referral for a colonoscopy or a flexible sigmoidoscopy procedure.

Indicator 172f, entitled "Medicare Bill", indicates that the patient has Medicare insurance, and that the staff will be alerted to this in order to appropriately order certain tests or labs that require certain Medicare specific guidelines. Indicator 172g, entitled "Insurance Bill", indicates that the physician may choose to allow the laboratory company to bill the insurance company directly for any lab tests or procedures, and that the medical office staff will be alerted so that they can follow the procedures for this. Indicator 172h, entitled "Labs done different day", indicates that the patient will need to come back another day to have lab tests performed, for example when the patient is in a fasting state, etc. Indicator 172h indicates that a nurse will be alerted to advise the patient to either come back to the office, or go to a laboratory for tests on a different day. Indicator 172i, entitled "Cigna Insurance", and indicator 172j, entitled "United Insurance", indicate that the patient is associated with third party insurance companies that disallow the medical office from billing directly to the insurance companies for lab tests performed. For example, these insurance companies may have an agreement directly with the laboratory companies and, therefore, indicators 172i, 172j indicate that the nurse and/or staff will be made aware of these specific insurance companies and their particular requirements.

GUI 170 also includes GUI control 114, entitled "Code Blue" (described in detail below) and GUI control 124, entitled "Return to Main Menu", that, when activated, returns the user to GUI 110 (FIG. 3).

Referring back to FIG. 3, GUI control 112f, entitled "Send Order", is configured to send to a nurse station computer 18 the information (i.e., a patient examination summary) collected/generated via the above-described GUIs (e.g., GUIs 120, 130, 140, 150, 160 and 170) when activated by the physician. The sent order includes all of the additional steps that need to be taken for a particular patient: diagnostic tests to be performed, drug samples to be given to the patient, referrals to specialists, educational material to be given to the patient, etc.

The patient examination summary is sent wirelessly to a nurse station computer 18 where an indicator button will show up on the nurse station screen showing that a new message order is waiting. There may also be an audible chime that alerts the nurse that a message order was sent. According to embodiments of the present invention, a physician may, retrieve an order entry sent to a nurse station 18, regardless of whether the order was completed and closed. Additional items may be added to the original order and resubmitted to the nurse station 18.

Figure 10A:
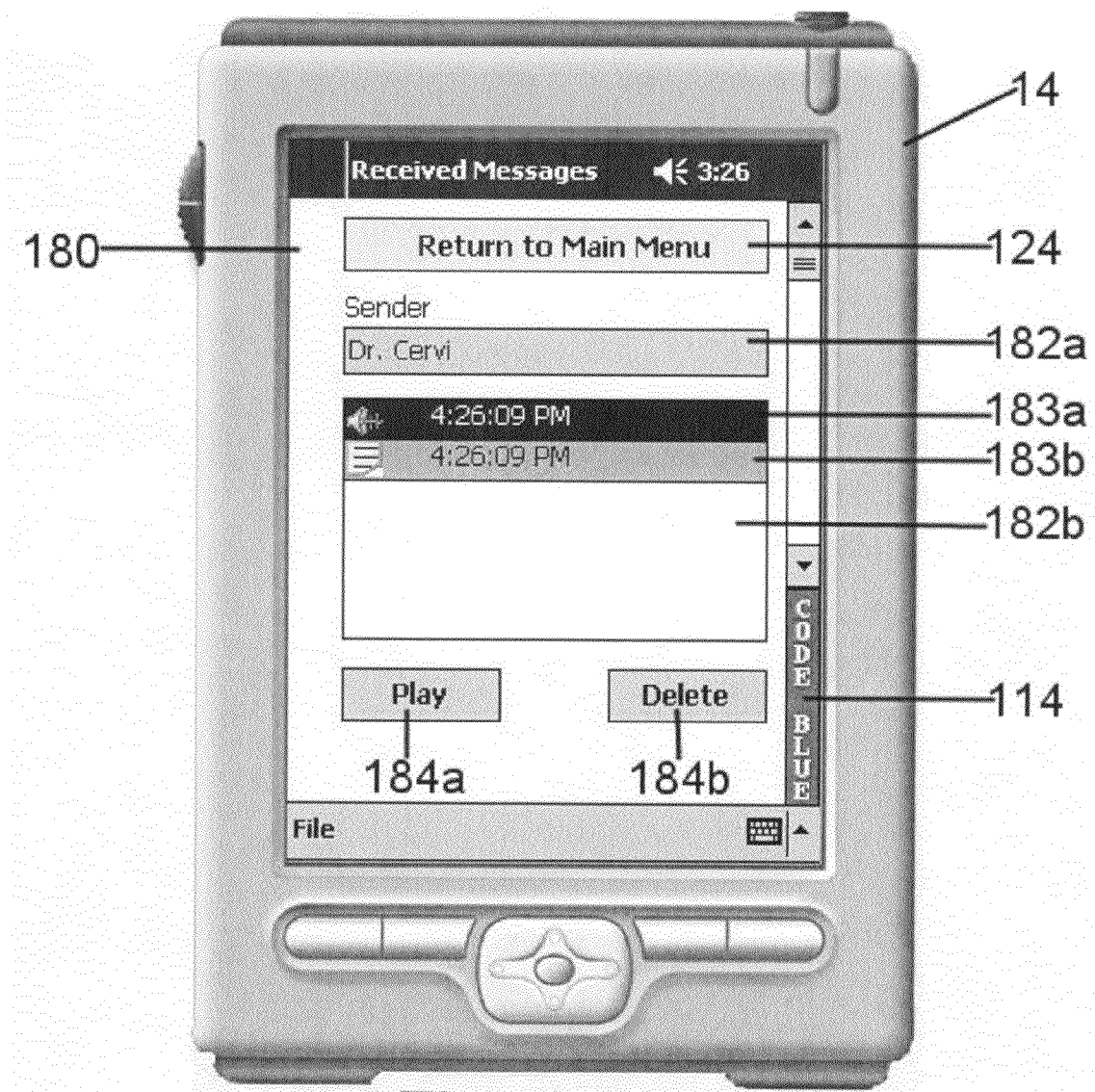
Figure 10B:
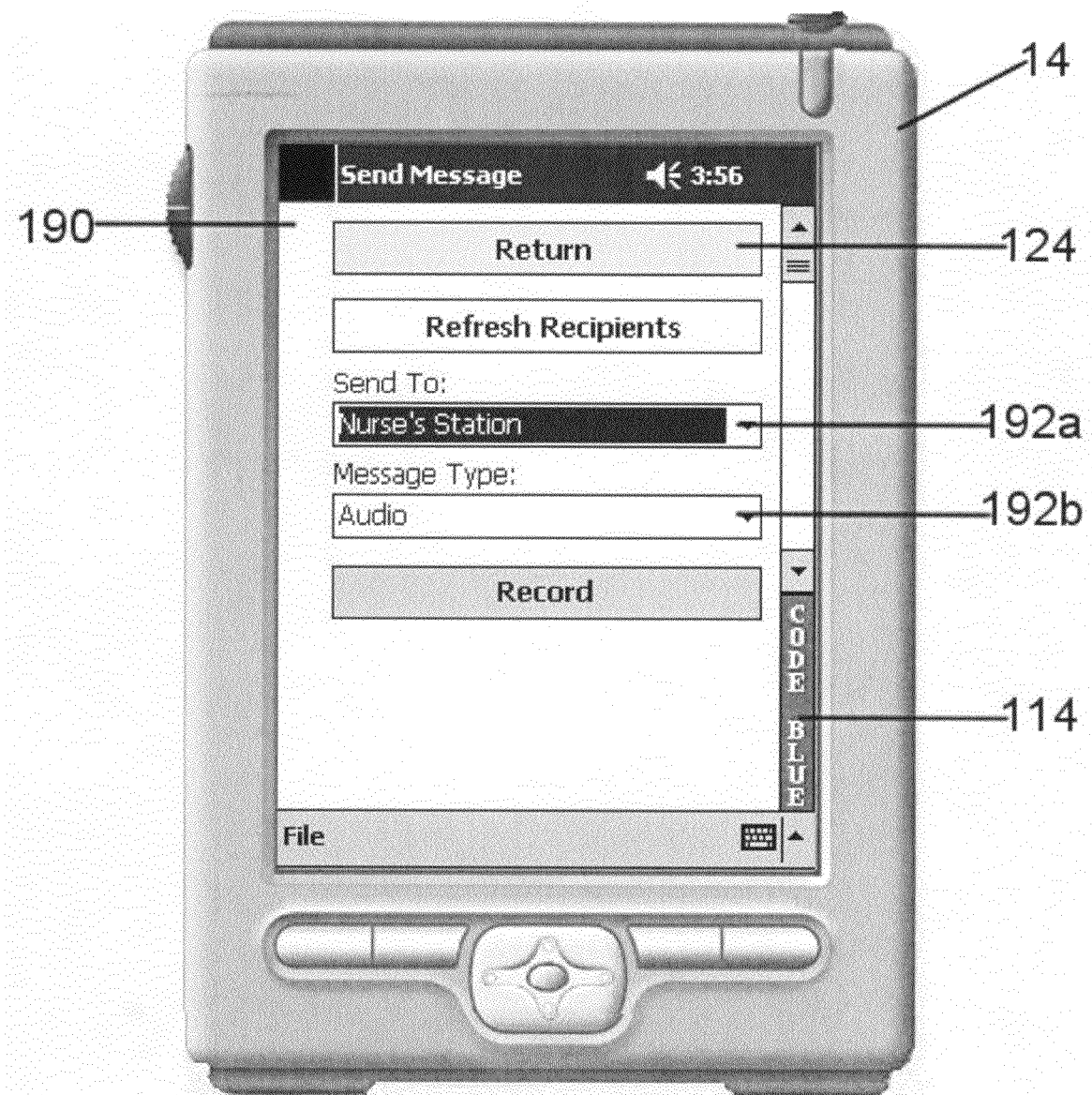

The eFlag software application executing on each handheld device 14, nurse station computer 18, and reception station computer 16 has a "communicator" function that facilitates audio and text communications between devices on the eFlag network 10. GUI 110 in FIG. 3 includes GUI control 112g, entitled "Check messages" and GUI control 112h, entitled "Send message" that control audio and/or text communications on a handheld device 14. FIG. 10A shows a GUI 180 on a handheld device which allows a physician to choose recipients of a message, and to choose whether to send an audio and/or text message. When GUI control 112g of GUI 110 is activated, GUI 180 is displayed. In the illustrated GUI 180, the sender's name is shown in GUI control 182a. Time stamped messages are displayed in GUI control 182b. The icon to the left of each time-stamped message indicates whether an audio 183a or text message 183b was sent. Messages sent via the communicator function of the present invention can be stored for later retrieval. When GUI control 112h of GUI 110 is activated, GUI 190 (FIG. 10B) is displayed. In the illustrated GUI 190, the recipient of a message can be selected from list box 192a and the type of message (i.e., audio or text) can be selected from list box 192b.

At the top of illustrated GUI 180 is a text box 182a indicating where a message was sent from, and a list box 182b that shows an example of an incoming audio message 183a and text message 183b. When an audio message 183a is highlighted, GUI controls 184a entitled "Play" and 184b entitled "Delete" are shown. If the incoming message is a text message 183b, GUI control 184a would be replaced with a GUI control entitled "Read". GUI 180 also includes GUI control 114, entitled "Code Blue" (described in detail below) and GUI control 124, entitled "Return to Main Menu", that, when activated, returns the user to GUI 110 (FIG. 3).

According to some embodiments of the present invention, the eFlag software application executing on each handheld device 14 is configured to allow physicians to perform dictation, store the dictation as an audio file, and send the audio files to a computer storage folder of choice on a device connected to the network 10. These audio files can be transmitted either by asynchronous or synchronous communication, as would be understood by those of skill in the art.

According to some embodiments of the present invention, the eFlag software application executing on each handheld device 14 is configured to allow physicians to send emails to other physicians via the web. For example, various information including, but not limited to, patient medications, laboratory tests, patient referrals, etc., can be emailed and in encrypted format. A physician receiving such an email would need the eFlag software application executing on a device in order to decrypt and read the emailed information, whether it was a text or audio file.

Figure 11:
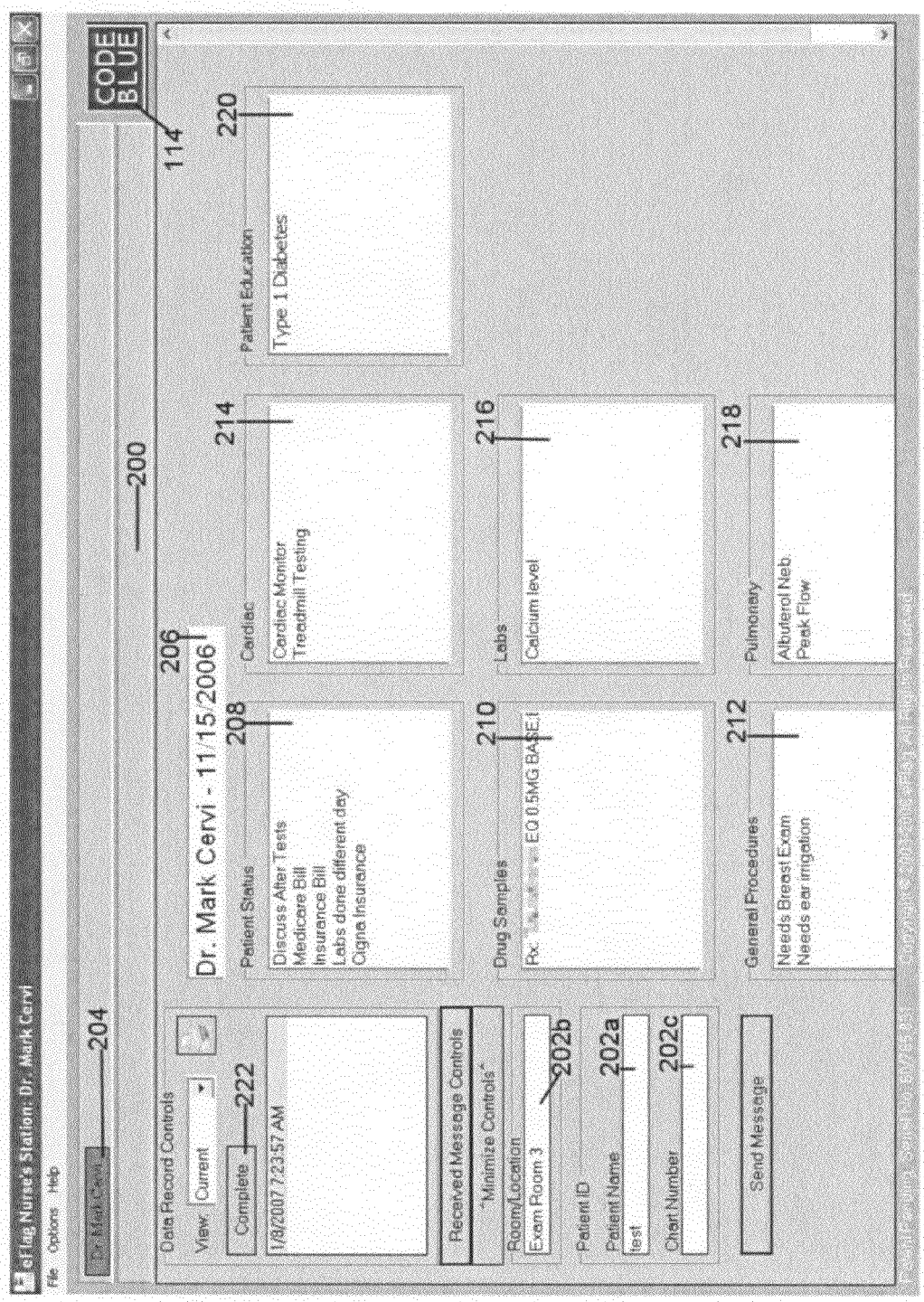
FIGS. 11-13 illustrate various GUIs that are displayed via a nurse station computer, according to some embodiments of the present invention.

Referring now to FIG. 11, the eFlag software application executing at a nurse station computer 18 displays GUI 200 when an order (i.e., patient examination summary) is received from a handheld device 14 as described above. All the various menu items are displayed on one screen for efficiency and ease of use. Each of the various categories are displayed in a compartmentalized manner (i.e., Cardiac, Labs, etc.). This eliminates the need for a nurse to scroll through multiple window screens to obtain the information from the physician.

The illustrated GUI 200 shows the patient name (GUI control 202a), patient location (GUI control 202b), and chart number (GUI control 202c). Along the top of the illustrated GUI 200 in area 204, the names of physicians logged on to the eFlag network 10 in a medical office can be displayed. A highlighted or otherwise indicated physician name in area 204 indicates to the nursing staff which physician sent a received order. The physician name is also displayed in area 206 along with the current date.

All of the information sent by a physician is displayed in GUI 200 in a very organized and compartmentalized fashion. A nurse will not have to go through a series of other windows, but will be able to identify all the necessary diagnostic tests and lab orders to be performed within a single user interface (i.e., GUI 200). For example, "Patient Status" information is displayed in area 208, drug sample information is displayed in area 210, information about procedures to be performed on a patient is displayed in area 212, cardiac information is displayed in area 214, laboratory information is displayed in area 216, pulmonary information is displayed in area 218, and patient education information is displayed in area 220.

Within GUI 200 are other GUI controls, including a GUI control 222, entitled "Complete", that the nurse activates after reviewing an order from a physician. Once the GUI control 222 has been activated, the information is then stored in a database for future retrieval or auditing purposes.

Figure 12:
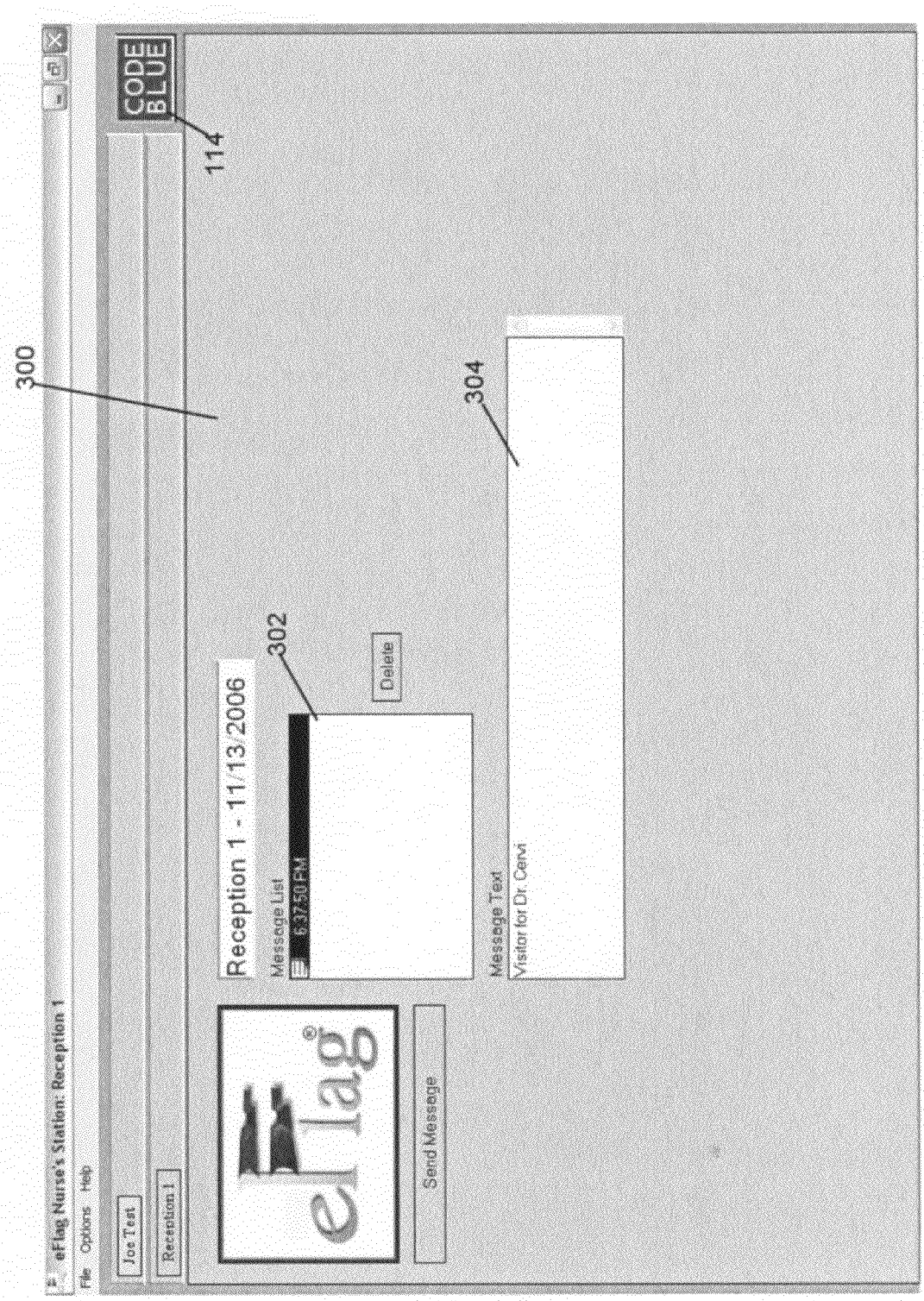

Referring to FIG. 12, GUI 300 illustrates the receipt of a message from a handheld device 14 by a nurse station computer 18 or by a reception station computer 16, according to some embodiments of the present invention. In the illustrated GUI 300, a time stamped message is initially highlighted in Message List box 302, and the text message appears in the Message Text box 304. To the left of the incoming message in Message List box 302 is an icon either indicating a text message (as shown), or may show an icon for a speaker indicating an audio message.

Figure 13:
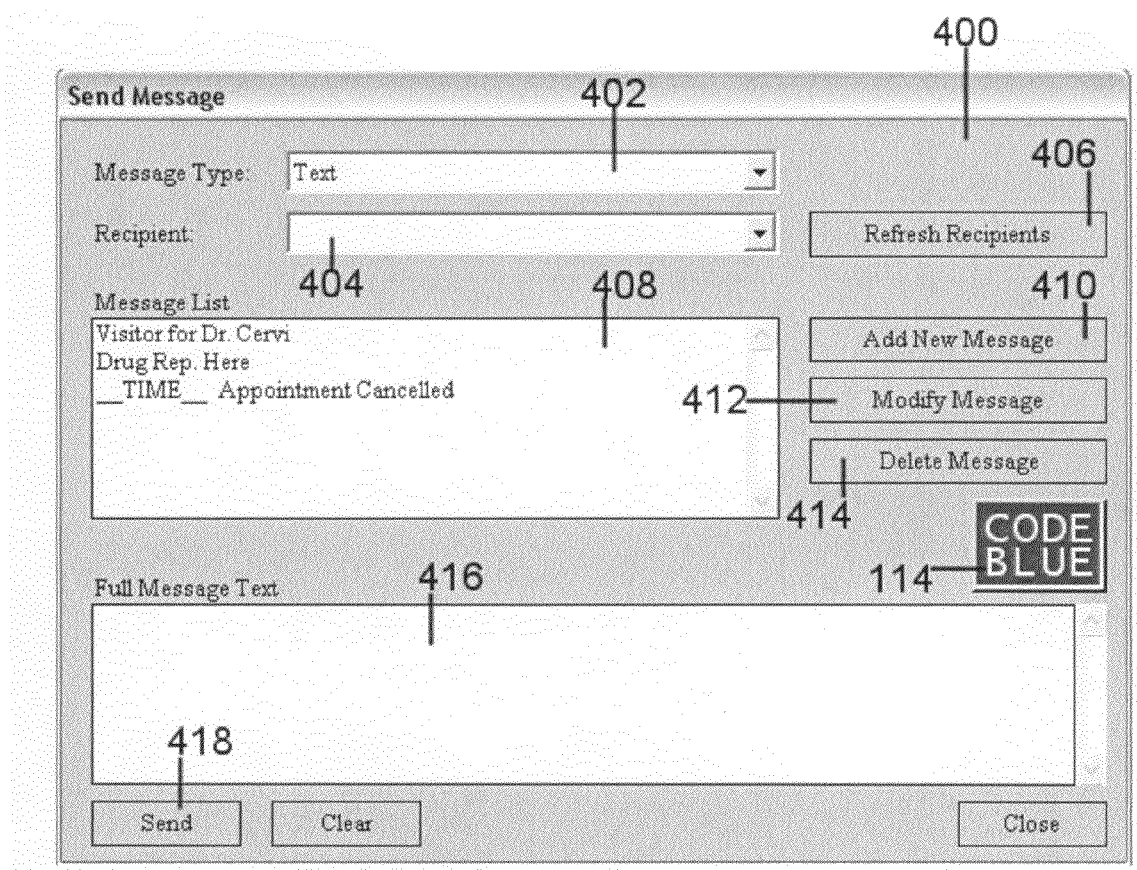

Referring to FIG. 13, GUI 400 illustrates the sending of a message from a handheld device 14, from a nurse station computer 18, or from a reception station computer 16, according to some embodiments of the present invention. In the illustrated GUI 400, the type of message is selected via GUI control 402, which contains a selectable list of message types. Options include, but are not limited to; text, high priority text, audio, and high priority audio. GUI control 404 is used to indicate to whom the outgoing message is intended, and contains a selectable list of recipients. Recipients in a displayed list in GUI control 404 include every handheld device 14, nurse station computer 18, reception station computer 16, or other computer in the network 10 of FIG. 1 which is logged on. In the illustrated GUI 400, GUI control 406, entitled "Refresh Recipients", can be activated in the event that a network device logged off and back on and was not shown immediately in the recipients drop-down box (GUI control 404). User activation of GUI control 406 will immediately bring such a network device back into view.

In the illustrated GUI 400, Message List box 408 can be customized to each individual network device and can be configured to hold the most commonly used text messages sent by a respective network device. GUI 400 includes additional GUI controls to create a new text message (GUI control 410), to modify an existing message (GUI control 412), or to delete an existing message (GUI control 414). If someone wishes to type a message only to send once, than free hand text can be entered via Full Message Text box 416 and sent without having to save the message. Once the desired message is either chosen via Message List box 408, or typed into the Full Message textbox 416, GUI control 418, entitled "Send" is activated to send the message.

Figure 14:
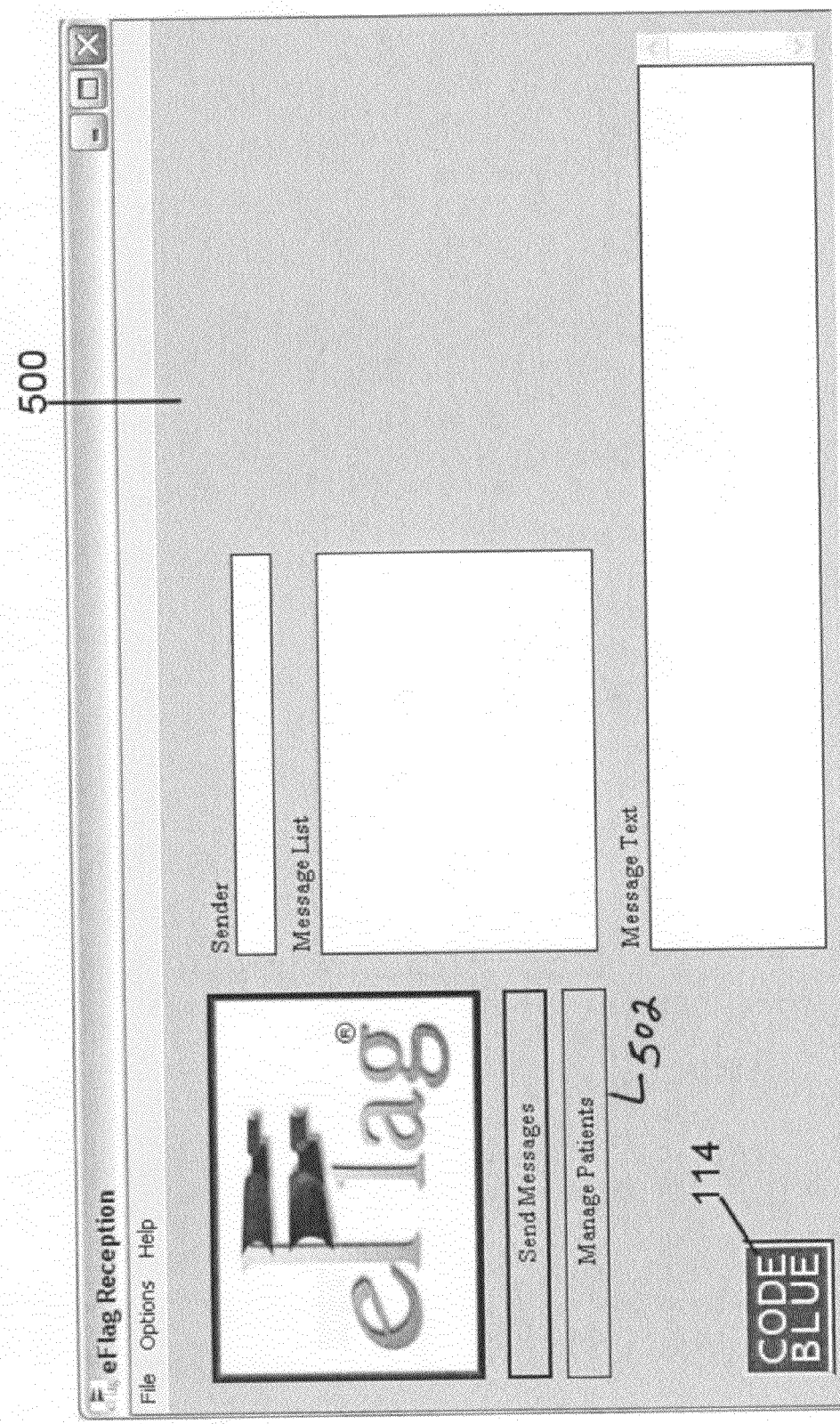
Figure 15:
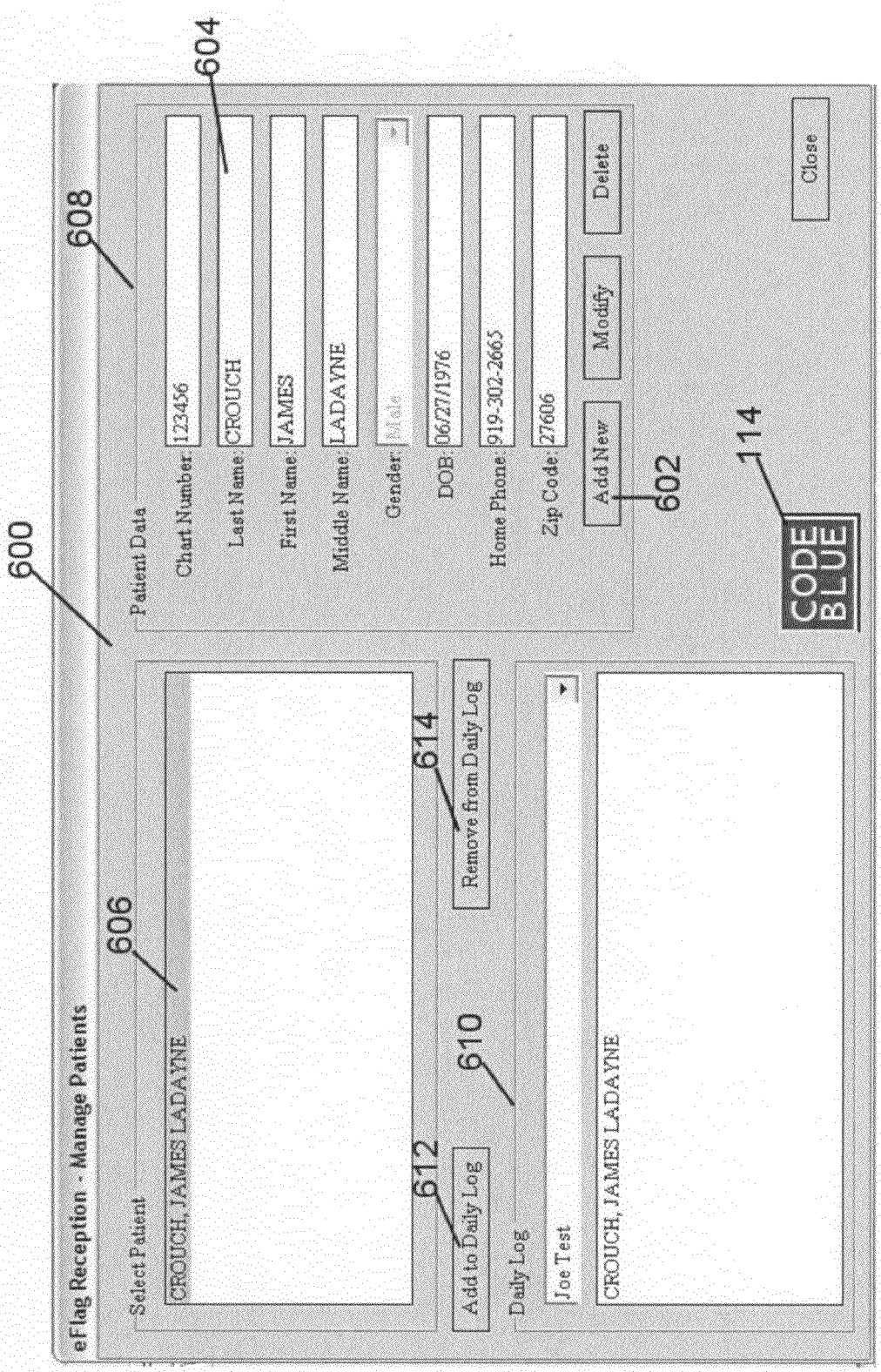

Referring to FIG. 14, GUI 500 is utilized by a reception station computer 16 to send messages and manage patients, according to some embodiments of the present invention. Messages are sent via GUI 500 as described above with respect to GUI 300, and need not be described again. GUI control 502, entitled "Manage Patients", is configured to display GUI 600, illustrated in FIG. 15, which allows a person at a reception station computer 16 to manage information about patients. Via GUI 600, patient demographic information is entered and stored in a database for future retrieval. As a patient checks into a medical office, a staff member pulls up the patient's name, and adds the patient into the daily log for a physician. The names within the daily log are always displayed on the physician's handheld device 14 for easy visualization. Patient names can be placed into the daily logs of multiple physicians, depending on which physician is seeing a particular patient for a visit.

Figure 16:
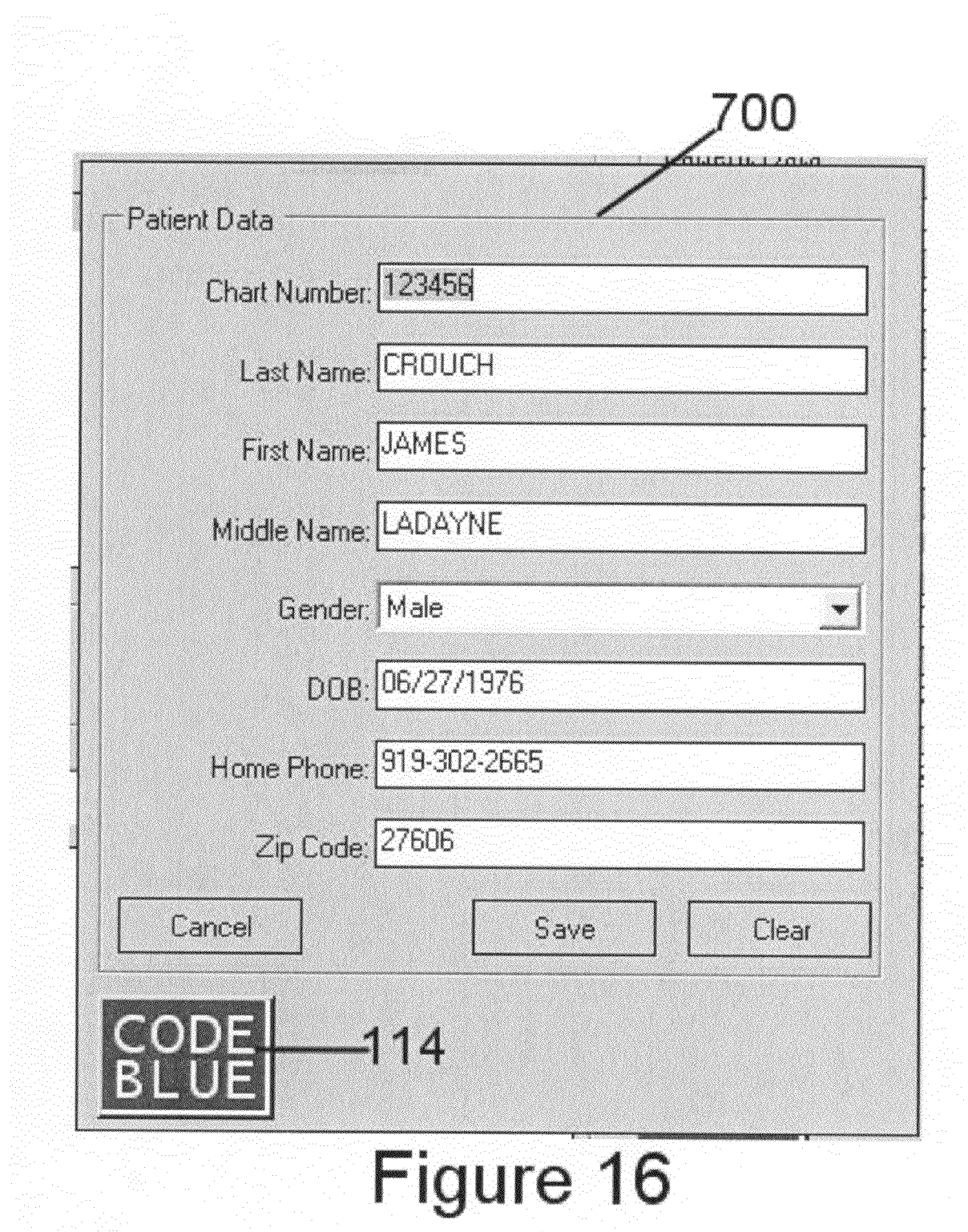

Several options are available via GUI 600. For example, if a patient is new to a medical practice, GUI control 602, entitled "Add New", is activated which displays GUI 700 in FIG. 16. Via GUI 700, the appropriate demographic information (e.g., chart number, name, gender, date of birth, telephone number, zip code, etc.) can be entered for a new patient as he/she checks in. Once the information is entered, it remains in a reception station computer database (or other accessible database) for future retrieval.

Referring back to FIG. 15, if a patient is an established patient of the medical practice and patient information is already entered into the database, a receptionist can quickly and easily type the first several characters of the patient's last name in the Last Name text box 604, and the database will begin to auto-scroll those names based on the length of characters entered. The list of names being auto-scrolled will appear within the Select Patient text box 606. The receptionist highlights that name in Select Patient text box 606 and demographic information from the patient will appear in Patient Data text box 608.

Once a patient name has been chosen, the patient's information can be added into the Patient Daily Log box 610 by activating GUI control 612, entitled "Add to Daily Log". The patient name then appears in the Daily Log box 610, and is the same information that a corresponding physician will see in the patient daily log (122c, FIG. 4) on his/her handheld device 14. Conversely, if a patient's name was already added to the daily log of patients to be seen by a respective physician, the patient name can also be removed from the daily log if the patient fails to keep his/her appointment via GUI control 614, entitled "Remove from Daily Log". Activation of GUI control 614 will remove a patient name from a physician's patient daily log (122c, FIG. 4) on his/her handheld device 14. In GUI 600, names in the Daily Log box 610 are arranged alphabetically. This has been determined to save more time for a physician than to list patient names in the order in which the names were added to the daily log. However, patient names may be arranged in various other ways, as well.

Figure 17:
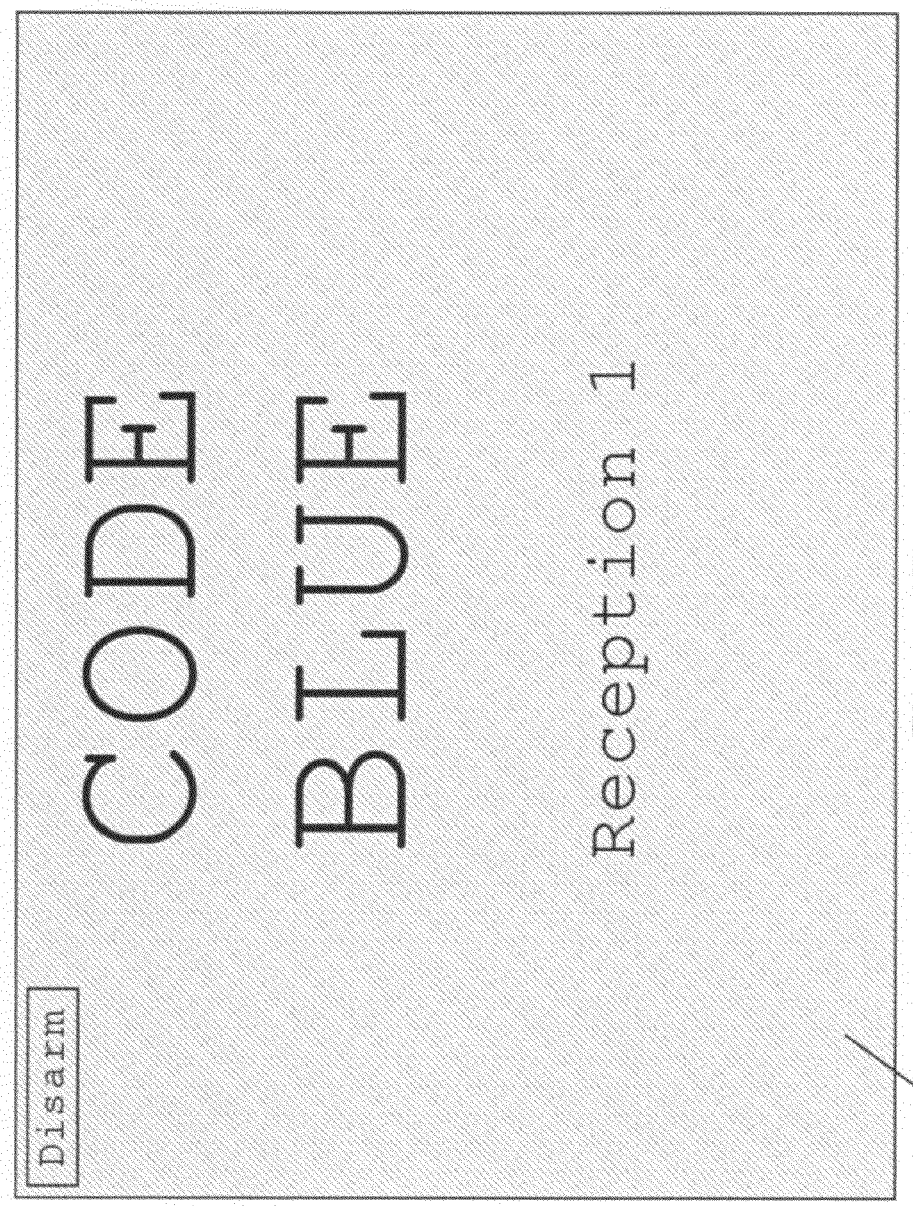
FIG. 17 illustrates a "Code Blue" display of emergency information, according to some embodiments of the present invention.

According to embodiments of the present invention, each handheld device 14, reception station computer 16, and nurse station computer 18 in the eFlag network 10 of FIG. 1 have the capability of dispatching a "Code Blue" to anyone connected to the communications network 10. Each desktop screen has a GUI control 114, entitled Code Blue (e.g., see GUIs 110, 120, 130, 140, 150, 160, 170, 180, 200, 300, 400, 500, 600, 700). When GUI control 114 is activated on any device, the Code Blue screen 800 illustrated in FIG. 17 is immediately displayed on all devices on the network. The "Code Blue" screen 800 also displays the location of the emergency for rapid response time, and a harsh audio sound may also sound to notify staff members not directly in front of their computers or near their handheld devices. In some embodiments of the present invention, Code Blue GUI controls 114 are provided on each and every GUI of the handheld devices 14 and nurse station computer 18 so that a Code Blue can be initiated at any time.

According to some embodiments of the present invention, when the Code Blue screen 800 illustrated in FIG. 17 is displayed on any device on the network, the device is rendered unusable until the medical emergency has been responded to and the device activating the Code Blue has deactivated the Code Blue. In large medical office settings where the locations of examination rooms can be widespread, it can be advantageous to be able to quickly notify medical personnel of the exact location of an emergency. When activated, all stations and handheld devices will automate the Code Blue similar to a fire alarm, and display the location from which the Code Blue was activated. Only the station which activated the alarm will have master control to disable all stations, but any non-medical personnel can disarm their respective station/handheld device without affecting other responding station personnel.

Embodiments of the present invention provide various marketing opportunities for companies such as pharmaceutical companies, office or clinical supply companies, vaccine companies, etc. to advertise branded products. The present invention uses an updater/launcher program that will automatically ping a designated website and query for any new or additional changes to be displayed on the various GUIs of devices connected to an eFlag network 10. Thus, company brand graphical logos can be strategically placed on desktop and/or handheld device GUIs for specified periods of time.

Figure 18:
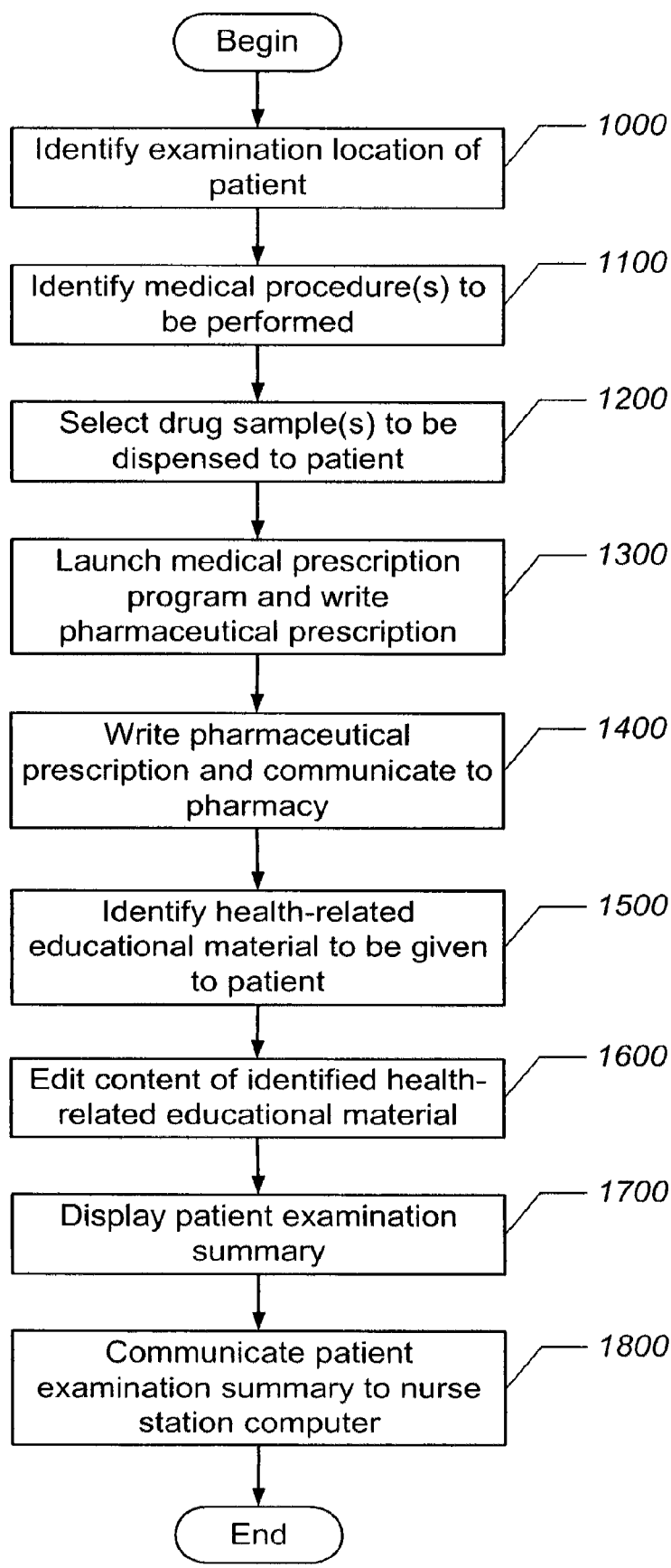
FIG. 18 is a flow chart that illustrates operations for facilitating patient examinations in a medical office, according to some embodiments of the present invention.

FIG. 18 is a flow chart that illustrates operations for facilitating patient examinations in a medical office, according to some embodiments of the present invention. Utilizing a handheld device executing the eFlag software application as described above, a physician identifies an examination location of a patient (Block 1000), and then identifies one or more medical procedures to be performed (Block 1100). As described above, identified medical procedures include, but are not limited to, laboratory analysis of biological samples obtained from the patient, diagnostic tests on the patient, patient vaccinations and/or injections, and preparing a medical prescription. The physician can select one or more drug samples to be dispensed to the patient (Block 1200).

According to some embodiments of the present invention, the physician can launch a third party medical prescription program and write a pharmaceutical prescription for the patient via the third party medical prescription program (Block 1300). According to some embodiments of the present invention, the physician can write a pharmaceutical prescription for the patient and communicate the prescription to a pharmacy external to the medical office via the handheld device (Block 1400).

According to some embodiments of the present invention, the physician can identify health-related educational material to be given to the patient and communicate the identified educational material to the nurse station computer (or other network device) for delivery to the patient and/or print the information directly from a handheld device (Block 1500). The physician may also be able to edit content of the identified health-related educational material prior to giving same to a patient (Block 1600).

The physician can display a patient examination summary on the handheld device (Block 1700). A displayed summary includes patient identification information, patient location information, patient health status information, a list of identified medical procedures, a list of drug samples given to the patient, information about prescriptions given to the patient, information about referrals to other specialists, information about health-related educational material to be given to the patient, etc. The patient examination summary is communicated, for example wirelessly, to a nurse station computer within the medical office (Block 1800). Initiation of a Code Blue is available in any of Blocks 1000-1800.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of facilitating an examination of a patient in a medical office, the method comprising the following performed via a handheld device:

displaying a first graphical user interface (GUI) within a display of the handheld device, wherein the first GUI comprises a plurality of GUI controls;

displaying a second GUI within the display in response to activation of a first GUI control in the first GUI by a physician, wherein the second GUI identifies an examination location of the patient within the medical office;

returning to the first GUI and displaying a third GUI within the display in response to activation of a second GUI control in the first GUI by the physician, wherein the third GUI includes a plurality of GUI controls, each associated with a respective medical procedure that can performed on the patient, and wherein each GUI control in the third GUI can be activated by the physician to select the respective medical procedure to be performed on the patient, wherein the medical procedures include laboratory analysis of biological samples obtained from the patient, diagnostic tests on the patient, and patient vaccinations and/or injections;

returning to the first GUI and displaying a patient examination summary in response to activation of a third GUI control in the first GUI by the physician, wherein the displayed summary includes patient identification information, patient location information, patient health status information, and a list of medical procedures selected by the physician to be performed on the patient; and communicating the patient examination summary to a computer within the medical office in response to activation of a fourth GUI control in the first GUI by the physician.

2. The method of claim 1, further comprising displaying a fourth GUI within the display in response to activation of a fifth GUI control in the first GUI by the physician, wherein the physician can select a drug sample to be dispensed to the patient and add an identification of the selected drug sample to the examination summary via the fourth GUI.

3. The method of claim 1, further comprising launching a third party medical prescription program within the handheld device within which the physician can write a pharmaceutical prescription for the patient.

4. The method of claim 1, further comprising writing a pharmaceutical prescription for the patient via the handheld device and communicating the prescription to a pharmacy external to the medical office in response to user activation of the fourth GUI control.

5. The method of claim 1, further comprising displaying a fifth GUI within the display in response to activation of a sixth GUI control in the first GUI by the physician, wherein the physician can select health-related educational material to be given to the patient and add an identification of the selected educational material to the examination summary via the fifth GUI.

6. The method of claim 5, further comprising editing content of the selected health-related educational material via the fifth GUI prior to adding an identification of the selected educational material to the patient examination summary.

7. The method of claim 5, further comprising printing the selected health-related educational material via a printer in communication with the handheld device.

8. The method of claim 1, wherein the second GUI comprises a plurality of GUI controls, each associated with a respective examination room in the medical office, and wherein physician activation of a GUI control in the second GUI displays an identification of the room in which the patient is located.

9. The method of claim 1, wherein communicating the patient examination summary to the computer comprises wirelessly communicating the patient examination summary.

10. A handheld device that facilitates an examination of a patient in a medical office, comprising:
   a processor;
   memory coupled to the processor; and
   computer program code residing in the memory that, when executed by the processor, causes the processor to perform the following:
   display a first graphical user interface (GUI) within a display of the handheld device, wherein the first GUI comprises a plurality of GUI controls;
   display a second GUI within the display in response to user activation of a first GUI control in the first GUI, wherein the second GUI identifies an examination location of the patient within the medical office;
   display a third GUI within the display in response to user activation of a second GUI control in the first GUI, wherein the third GUI includes a plurality of GUI controls, each associated with a respective medical procedure than can be performed on the patient, and wherein each GUI control in the third GUI can be activated to select the respective medical procedure to be performed on the patient, wherein the procedures include laboratory analysis of biological samples obtained from the patient, diagnostic tests on the patient, and patient vaccinations and/or injections;
   display a patient examination summary in response to user activation of a third GUI control in the first GUI, wherein the displayed summary includes patient identification information, patient location information, patient health status information, and a list of medical procedures selected by the user to be performed on the patient; and
   communicate the patient examination summary to a computer within the medical office in response to user activation of a fourth GUI control in the first GUI.

11. The device of claim 10, further comprising computer program code residing in the memory that, when executed by the processor, retrieves a patient examination summary from the computer and allows a user to modify the retrieved patient examination summary.

12. The device of claim 10, further comprising computer program code residing in the memory that, when executed by the processor, displays a fourth GUI within the display in response to user activation of a fifth GUI control in the first GUI, wherein a drug sample to be dispensed to the patient can be selected and an identification of the selected drug sample added to the examination summary via the fourth GUI.

13. The device of claim 12, further comprising computer program code residing in the memory that, when executed by the processor, communicates information about the selected drug sample to an external third party in response to user activation of the fourth GUI control.

14. The device of claim 10, further comprising computer program code residing in the memory that, when executed by the processor, launches a third party medical prescription program within the handheld device within which a pharmaceutical prescription can be written by a user for the patient.

15. The device of claim 10, further comprising computer program code residing in the memory that, when executed by the processor, allows a user to write a pharmaceutical prescription for the patient and communicate the prescription to a pharmacy external to the medical office.

16. The device of claim 10, further comprising computer program code residing in the memory that, when executed by the processor, displays a fifth GUI within the display in response to user activation of a sixth GUI control in the first GUI, wherein the user can select health-related educational material to be given to the patient and add an identification of the selected educational material to the examination summary via the fifth GUI.

17. The device of claim 16, further comprising computer program code residing in the memory that, when executed by the processor, allows a user to edit content of the selected health-related educational material via the fifth GUI.

18. The device of claim 16, further comprising computer program code residing in the memory that, when executed by the processor, prints the identified educational material via a printer in communication with the handheld communications device.

19. The device of claim 10, further comprising computer program code residing in the memory that, when executed by the processor, displays an identification of the room in which the patient is located.

20. The device of claim 10, further comprising computer program code residing in the memory that, when executed by the processor, wirelessly communicates the patient examination summary.

21. The device of claim 10, further comprising computer program code residing in the memory that, when executed by the processor, securely communicates directly with third party health care providers.

22. The device of claim 10, further comprising computer program code residing in the memory that, when executed by the processor, receives advertisements from external third parties and displays received advertisements within the display.

23. The device of claim 10, further comprising computer program code residing in the memory that, when executed by the processor, displays a third party referral form within the display.

24. A medical office system that facilitates patient examinations, comprising:
   a nurse station computer; and
   one or more handheld devices, wherein each handheld device communicates wirelessly with the nurse station computer, and wherein each handheld device comprises:
   a processor;
   memory coupled to the processor; and
   computer program code residing in the memory that, when executed by the processor, causes the processor to perform the following:
   display a first graphical user interface (GUI) within a display of the handheld device, wherein the first GUI comprises a plurality of GUI controls;
   display a second GUI within the display in response to user activation of a first GUI control in the first GUI, wherein the second GUI identifies an examination location of the patient within the medical office;
   display a third GUI within the display in response to user activation of a second GUI control in the first GUI, wherein the third GUI includes a plurality of GUI controls, each associated with a respective medical procedure than can be performed on the patient, and wherein each GUI control in the third GUI can be activated to select the respective medical procedure to be performed on the patient, wherein the procedures include laboratory analysis of biological samples obtained from the patient, diagnostic tests on the patient, and patient vaccinations and/or injections;

display a patient examination summary in response to user activation of a third GUI control in the first GUI, wherein the displayed summary includes patient identification information, patient location information, patient health status information, and a list of identified medical procedures selected by the user to be performed on the patient; and communicate the patient examination summary wirelessly to the nurse station computer in response to user activation of a fourth GUI control in the first GUI.

25. The system of claim 24, wherein each handheld device communicates wirelessly with any other handheld device.

26. The system of claim 24, further comprising a patient reception computer that receives and stores patient demographic information, wherein the patient reception computer communicates wirelessly with the nurse station computer and with each handheld device.

27. The system of claim 24, wherein each handheld device displays a daily log of patients to be examined by a physician, and wherein the patient reception computer adds patients checking in at the medical office to a physician's daily log.

28. The system of claim 24, wherein each handheld device displays emergency information transmitted by another handheld device or by the nurse station computer, and wherein the emergency information identifies the location of the emergency within the medical office.

29. The system of claim 28, wherein each handheld device sounds an audio alert in response to receiving emergency information transmitted by another handheld device or by the nurse station computer.

30. The system of claim 24, wherein the nurse station computer displays emergency information transmitted by a handheld device, and wherein the emergency information identifies the location of the emergency within the medical office.

31. The system of claim 24, wherein each handheld device records and stores dictation.

32. The system of claim 24, wherein each handheld device sends and receives voice and/or text communications.

33. The system of claim 24, wherein each handheld device sends and receives electronic mail.

34. The system of claim 24, wherein the nurse station computer and each handheld device communicate directly with a third party laboratory service and request medical laboratory work directly therefrom.

35. A computer program product for facilitating patient examinations in a medical office, comprising:

a computer readable storage medium tangibly embodying a program executable with computer instructions, wherein the computer instructions comprise means for enabling a processor to:

display a first graphical user interface (GUI) within a display of the handheld device, wherein the first GUI comprises a plurality of GUI controls;

display a second GUI within the display in response to user activation of a first GUI control in the first GUI, wherein the second GUI identifies an examination location of the patient within the medical office;

display a third GUI within the display in response to user activation of a second GUI control in the first GUI, wherein the third GUI includes a plurality of GUI controls, each associated with a respective medical procedure that can be performed on the patient, and wherein each GUI control in the third GUI can be activated to select the respective medical procedure to be performed on the patient, wherein the medical procedures include laboratory analysis of biological samples obtained from the patient, diagnostic tests on the patient, and patient vaccinations and/or injections;

display a patient examination summary in response to user activation of a third GUI control in the first GUI, wherein the displayed summary includes patient identification information, patient location information, patient health status information, and a list of medical procedures selected by the user to be performed on the patient; and communicate the patient examination summary to a computer within the medical office in response to user activation of a fourth GUI control in the first GUI.

36. The device of claim 10, further comprising computer program code residing in the memory that, when executed by the processor, receives information about a medical emergency within the medical office; and displays the received medical emergency information as a single alert in a single GUI that fills the display of the handheld device, wherein the emergency information in the single alert identifies the location of the emergency within the medical office, and wherein the handheld device is rendered unusable until the medical emergency has been responded to.

37. The device of claim 36, further comprising computer program code residing in the memory that, when executed by the processor, sounds an audio alert in response to receiving the medical emergency information.

* * * * *

UNITED STATES PATENT AND TRADEMARK OFFICE
CERTIFICATE OF CORRECTION

PATENT NO. : 8,204,760 B2
APPLICATION NO. : 11/701695
DATED : June 19, 2012
INVENTOR(S) : Cervi et al.

Page 1 of 1

It is certified that error appears in the above-identified patent and that said Letters Patent is hereby corrected as shown below:

In the Claims:
Column 18, Claim 1, Line 16-17: Please correct "procedure that can performed"
to read -- procedure that can be performed --

Column 19, Claim 10, Line 25: Please correct "dure than can be performed"
to read -- dure that can be performed --

Column 20, Claim 24, Line 61: Please correct "dure than can be performed"
to read -- dure that can be performed --

Signed and Sealed this
Twenty-third Day of April, 2013

Teresa Stanek Rea
*Acting Director of the United States Patent and Trademark Office*